(12) United States Patent
Syed et al.

(10) Patent No.: US 10,987,301 B2
(45) Date of Patent: Apr. 27, 2021

(54) METHODS AND COMPOSITIONS FOR TREATING DAMAGED HAIR

(71) Applicant: SALON COMMODITIES, INC., Melrose Park, IL (US)

(72) Inventors: Ali Naqi Syed, Oak Brook, IL (US); Anthony J. O'Lenick, Dacula, GA (US)

(73) Assignee: Salon Commodities, Inc., Melrose Park, IL (US)

(*) Notice: Subject to any disclaimer, the term of this patent is extended or adjusted under 35 U.S.C. 154(b) by 86 days.

(21) Appl. No.: 16/069,138

(22) PCT Filed: Jan. 15, 2017

(86) PCT No.: PCT/US2017/013612
§ 371 (c)(1),
(2) Date: Jul. 10, 2018

(87) PCT Pub. No.: WO2017/124061
PCT Pub. Date: Jul. 20, 2017

(65) Prior Publication Data
US 2019/0029945 A1 Jan. 31, 2019

Related U.S. Application Data

(60) Provisional application No. 62/279,438, filed on Jan. 15, 2016.

(51) Int. Cl.
| | |
|---|---|
| *A61Q 5/04* | (2006.01) |
| *A61K 8/892* | (2006.01) |
| *A61Q 5/00* | (2006.01) |
| *C08G 77/38* | (2006.01) |
| *C08L 83/06* | (2006.01) |
| *A61K 8/22* | (2006.01) |
| *A61K 8/23* | (2006.01) |
| *C08G 77/14* | (2006.01) |

(52) U.S. Cl.
CPC ............ *A61K 8/892* (2013.01); *A61K 8/22* (2013.01); *A61K 8/23* (2013.01); *A61Q 5/002* (2013.01); *C08G 77/38* (2013.01); *C08L 83/06* (2013.01); *A61K 2800/4324* (2013.01); *A61K 2800/882* (2013.01); *C08G 77/14* (2013.01)

(58) Field of Classification Search
None
See application file for complete search history.

(56) References Cited

U.S. PATENT DOCUMENTS

| | | | |
|---|---|---|---|
| 5,312,968 A | 5/1994 | O'Lenick, Jr. et al. | |
| 5,488,121 A | 1/1996 | O'Lenick, Jr. | |
| 5,989,533 A * | 11/1999 | Deegan | A61K 8/342 424/401 |
| 6,175,028 B1 * | 1/2001 | O'Lenick, Jr. | A61K 8/0295 528/25 |
| 2004/0158938 A1 | 8/2004 | Geary et al. | |
| 2006/0018867 A1 | 1/2006 | Kawasaki et al. | |
| 2013/0058880 A1 | 3/2013 | Dong | |
| 2015/0096584 A1 | 4/2015 | Washington et al. | |
| 2015/0305469 A1 | 10/2015 | Paul | |
| 2020/0022903 A1 | 1/2020 | Syed | |

FOREIGN PATENT DOCUMENTS

| | | |
|---|---|---|
| WO | WO 2009/061360 A1 | 5/2009 |
| WO | WO 2015/155047 A1 | 10/2015 |
| WO | WO 2017/124061 A1 | 7/2017 |

OTHER PUBLICATIONS

European Patent Office, Extended European Search Report in European Patent Application 17739124.0 (dated Aug. 2, 2019).
United States Patent and Trademark Office, International Search Report in International Application No. PCT/US2017/013612 (dated May 10, 2017).
United States Patent and Trademark Office, Written Opinion in International Application No. PCT/US2017/013612 (dated May 10, 2017).
International Bureau of WIPO, International Preliminary Report on Patentability in International Application No. PCT/US2017/013612 (dated Jul. 26, 2018).
Pubchem, Substance Record for SID 272710350, Available Date: Dec. 11, 2015 [retrieved on Jun. 21, 2018]. Retrieved from the Internet: <URL: https://pubchem.ncbi.nlm.nih.gov/substance/272710350>.
Pubchem, Substance Record for SID 252226016, Available Date: Sep. 1, 2015 [retrieved on Jun. 21, 2018]. Retrieved from the Internet: <URL: https://pubchem.ncbi.nlm.nih.gov/substance/252226016>.
U.S. Appl. No. 16/497,639, filed Sep. 25, 2019.

* cited by examiner

*Primary Examiner* — Susan T Tran
(74) *Attorney, Agent, or Firm* — Leydig, Volt & Mayer, Ltd.

(57) ABSTRACT

Provided is a method for treating hair damage by contacting the hair with an effective amount of an epoxysilicone. The method may be used for treating hair damage caused by a hair altering process that is capable of damaging hair, for example, hair lightening/bleaching procedures, hair relaxing procedures, hair dyeing procedures, hair permanent waving, and hair smoothing. Also provided is a composition and a product, which include a hair damage treating effective amount of the epoxysilicone.

52 Claims, 2 Drawing Sheets

METHODS AND COMPOSITIONS FOR TREATING DAMAGED HAIR

CROSS-REFERENCE TO RELATED APPLICATIONS

This patent application is the U.S. national stage of International Patent Application No. PCT/US2017/013612, filed on Jan. 15, 2017, which claims the benefit of U.S. Patent Application No. 62/279,438, filed Jan. 15, 2016, the disclosures of which are incorporated herein by reference in their entireties for all purposes.

BACKGROUND OF THE INVENTION

Human hair is regularly exposed to conditions that are damaging to the structure and integrity of hair fibers. Notably, many widely used cosmetic processes that are intended to alter the hair such as, for example, bleaching/lightening, relaxing, permanent coloring, permanent waving, and keratin smoothing procedures, involve treating the hair with strong oxidants, alkaline reagents, reducing agents and/or aldehyde compounds, in conjunction with heat, which can be damaging to hair fibers. Regular exposure to surfactants and detergents, such as those found in commercial shampoos, also can damage hair fibers. Human hair is also subjected to mechanical stresses such as, e.g., combing, brushing, and heat styling, which can damage hair fibers over time. Certain environmental conditions such as, for example, exposure to sunlight and oxygen, also can be damaging to hair fibers.

Hair altering procedures that damage hair have been in use for quite some time. For example, the bleaching or lightening of human hair has been widely practiced for centuries. The ancient Romans used to bleach their hair from beech ashes and tallow derived from goat fat, and Europeans of the medieval era used caustic soda solution and sunlight for the same purpose. Such processes involved exposing the hair to alkaline oxidative conditions, which are damaging to hair. Modern bleaching or lightening processes decolorize hair by an oxidation process carried out at an alkaline pH such as 9.5 to 11. Modern bleaching or lightening processes are employed either to lighten hair or to prepare the hair for a coloring process when a lighter shade is preferred over than the natural shade. A very common procedure involves lightening fibers in small bunches throughout the head to give a special affect. The result is hair with a higher tonal level relative to the natural tonal level. The extent of hair lightening may be evaluated on a tonal scale, e.g., from level 1, which is black hair, to level 12, which is lightest blond hair.

Virtually all conventional bleaching processes involve oxidation. Such processes give lighter shades, resulting in white or blond hair, depending on the time of application and the strength/amount of oxidant used (e.g., hydrogen peroxide). Such processes are very damaging to hair by causing a loss of strength/elasticity and an increase in fiber porosity, which is associated with hair damage. In some cases, the hair must be bleached twice in order to decolorize dark hair to a blonde shade. This bleaching process is regarded as a double process, and is extremely damaging to hair in terms of its elasticity and tensile strength, its moisture content, porosity, and split ends.

Bleaching/lightening processes typically involve applying a mixture of powder lightener and hydrogen peroxide developer. Modern hair straightening (sometimes referred to as relaxing) processes typically involve applying an alkali metal hydroxide or guanidine to the hair. Modern hair coloring processes typically involve applying oxidative dyes mixed with hydrogen peroxide (chemically altering the hair fibers permanently). Each of these procedures are reactive, and damage the hair significantly with respect to hair elasticity/tensile strength, porosity, susceptibility to damage caused by combing/brushing, and moisture content. The effect of repeated use of these products on the hair and scalp can be especially damaging to hair fibers. Even a single hair lightening procedure may, for example, reduce hair elasticity by 15-25%, and increase fiber porosity from, e.g., 31% (untreated hair) to 55% (treated) for bleached hair. If dark hair is double processed to make it blonde, the damage is even more severe.

Straightening (relaxing) processes are typically permanent processes in which hair is treated with a cream containing alkali metal hydroxides or guanidine for a period of 15 to 20 minutes. This process typically changes about one-third of cystine bonds of the treated hair fibers to lanthionine bonds. As a result, curly hair becomes permanently straight. When hair is subjected to such a straightening process, the hair can lose, for example, 30-60% of its tensile strength, and experience a significant loss of moisture content as well as a significant increase in porosity.

Permanent hair coloring processes are also reactive processes, and typically involve applying a mixture of hydrogen peroxide and one or more oxidative dyes to hair for a period of 45 minutes in order to alter the original color of the hair significantly. Such oxidative dyes typically include reducing agents such as sodium sulfite or sodium metabisulfite to stabilize dyeing creams from air oxidation. Such mixtures of oxidative dyes and hydrogen peroxide can reduce the tensile strength of hair fibers, for example, by 5-15% depending upon the dye and the amount of hydrogen peroxide used.

Permanent waving (or "perming") can involve treating hair fibers with alkaline solutions thioglycolic acid at a pH of 9.0 to 9.50. The cystine bonds of the hair fibers reduce to cysteine during the treatment, and the fibers are then wound onto a curler of choice to lock in the shape of the desired curls. After about 20 minutes the fibers are rinsed and treated with an oxidizing agent such as hydrogen peroxide or sodium bromate. The hair is then treated with a neutralizing agent such as a 2.0% solution of hydrogen peroxide at a pH of 3.5. During this process, hair fibers can swell and undergo a significant loss of fiber elasticity. The loss of elasticity during the perming process can be 20 to 25%, and the increase in porosity also can be significant. Although most of the cysteine bonds are reconverted to cystine during neutralizing (oxidation) with hydrogen peroxide, the reconversion is not complete, leaving behind unconverted cysteine bonds.

Keratin smoothing/straightening treatments involve modifying wavy, curly and super curly hair found among many races in the world. Such treatments can involve straightening the hair with heat appliances such as blow driers and flat irons, or permanently straightening the hair with chemically reactive products, such as hair relaxers based upon sodium/lithium hydroxide, guanidine hydroxide, or ammonium thioglycolate. Wavy or curly hair, when straightened with relaxers, readily becomes frizzy upon exposure to humidity. Permanent straightening treatments that involve the use of formaldehyde or glycolic acid involve subjecting the hair to high temperatures, e.g., 450° F. or 230° C., which can impart a significant degree of damage to hair, resulting in loses of 20-25% of its tensile strength. In addition, the use of formaldehyde in such treatments raises safety concerns.

Accordingly, there is a need for improved methods, compositions and products for treating hair damage associated with exposure to conditions or treatments that are damaging to hair, especially hair altering procedures such as, e.g., lightening/bleaching, relaxing, permanent coloring procedures, permanent waving, and keratin smoothing treatments. The present invention provides such methods, compositions and products.

BRIEF SUMMARY OF THE INVENTION

The present invention provides a method for treating hair damage, which method includes contacting the hair with an effective amount of an epoxysilicone preferably of formula (I) below:

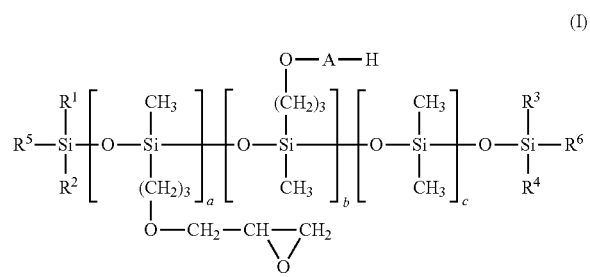

wherein $R^1$-$R^4$ are methyl; $R^5$ and $R^6$ are the same or different and each is preferably $C_{1-26}$ alkyl or a substituent of the formula:

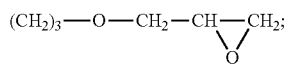

a is preferably from 0-20; b is preferably from 0-20; c is preferably from 0-30, and A is preferably selected from one or more of $(CH_2—CH_2—O)_x$, $(CH(CH_3)—CH_2—O)_y$, and $(CH_2—CH(CH_3)—O)_z$, wherein x, y, and z are the same or different and each is preferably from 0-20. When a is 0, then at least one of $R^5$ and $R^6$ is preferably a substituent of the formula:

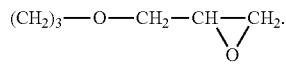

The method of the present invention may be used for treating hair damage caused by a hair altering process that is capable of damaging hair fibers. Such hair altering processes may include, for example, hair lightening/bleaching procedures, hair relaxing procedures, hair dyeing procedures, permanent waving, keratin smoothing treatments and the like. When the compound of formula (I) is used for treating hair damage caused by a hair altering process, the compound of formula (I) may be applied to the hair before, concurrently, or following application of the hair altering agent. If desired, the compound of formula (I) and hair altering agent may be combined together to form a composition containing the hair altering agent and an effective amount of the compound of formula (I) before application to the hair.

The present invention additionally provides a composition comprising a carrier and a hair damage treating effective amount of at least one compound of formula (I) as described herein. The composition of the present invention may further include a hair altering agent that is capable of damaging hair fibers. The carrier may include, for example, a liquid vehicle such as, for example, an aqueous liquid vehicle. If desired, the composition of the present invention may be formulated as a solution, e.g., an aqueous solution, or as an emulsion, e.g., an aqueous emulsion.

The present invention further provides a product, which includes a hair damage treating effective amount of at least one compound of formula (I) as described herein, and instructions for applying the compound of formula (I) to the hair. If desired, the compound of formula (I) may be formulated as a composition as described herein. The product of the present invention may further include a hair altering agent, combined with or contained separately from the compound of formula (I), and instructions for applying the hair altering agent to the hair. When the product of the present invention includes a hair altering agent, the instructions may include instructions for applying the compound of formula (I) before, concurrently, or following application of the hair altering agent to the hair. In one embodiment, the product of the present invention includes at least one compound of formula (I) as described herein, a hair altering agent, and instructions for combining the hair altering agent and the compound of formula (I) before application to the hair.

The compound of formula (I) may be combined or used in conjunction with one or more catalysts, which are preferably capable of enhancing epoxide reactivity. One or more of such catalysts may be included in or used in conjunction with the compositions and products of the present invention.

DETAILED DESCRIPTION OF THE INVENTION

Figure 1:
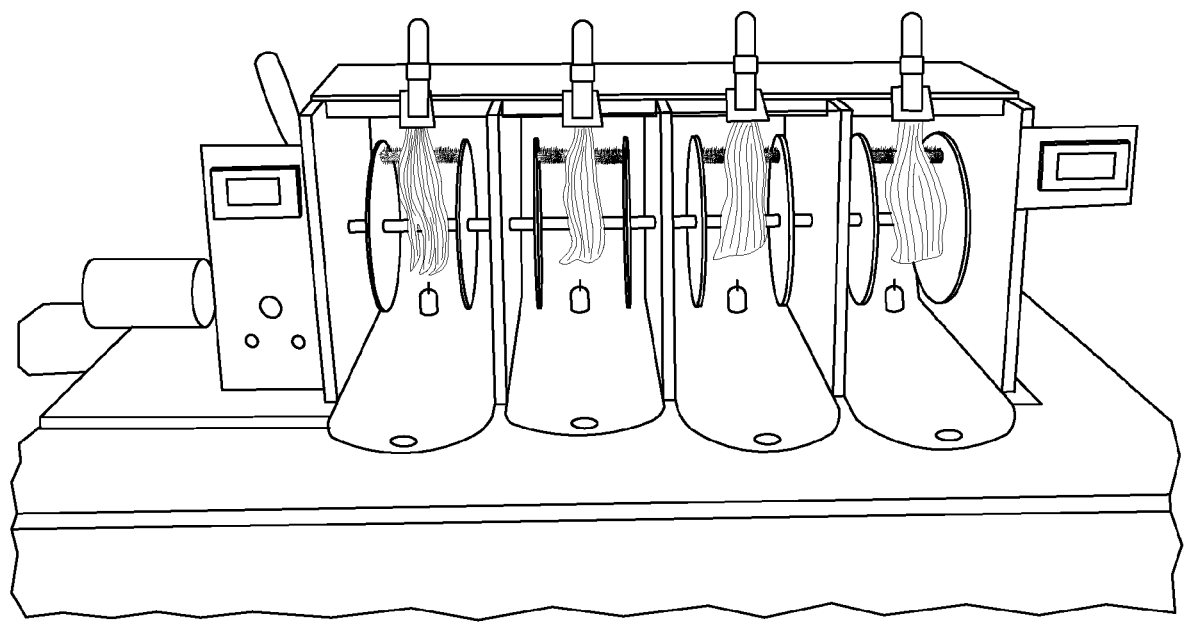
FIG. 1 depicts a device for simulating repeated combing/brushing on sample hair tresses.

The present invention provides a method for treating hair damage, which method includes contacting the hair with an effective amount of an epoxysilicone, which is preferably of formula (I):

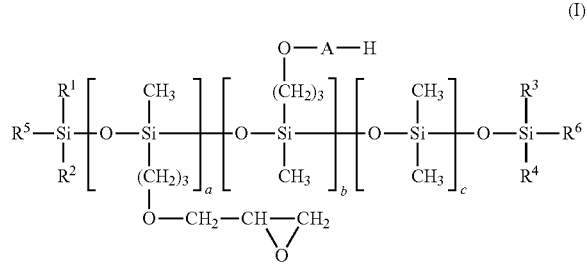

wherein $R^1$-$R^4$ are methyl; $R^5$ and $R^6$ are the same or different and each is preferably $C_{1-26}$ alkyl or a substituent of the formula:

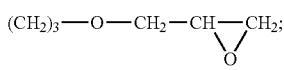

a is preferably from 0-20; b is preferably from 0-20; c is preferably from 0-30, and A is preferably selected from one or more of $(CH_2-CH_2-O)_x$, $(CH(CH_3)-CH_2-O)_y$, and $(CH_2-CH(CH_3)-O)_z$, wherein x, y, and z are the same or different and each is preferably from 0-20. When a is 0, then at least one of $R^5$ and $R^6$ is preferably a substituent of the formula:

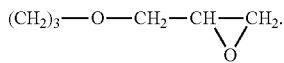

The epoxysilicone used in accordance with the present invention includes at least one epoxide-containing substituent. Thus, when a compound of formula (I) is used, and a is 0, then at least one of $R^5$ and/or $R^6$ desirably includes an epoxide-containing substituent, which is preferably of the formula:

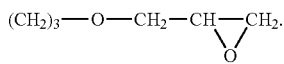

Similarly, when a compound of formula (I) is used, and both $R^5$ and $R^6$ are $C_{1-26}$ alkyl, then a is preferably at least 1.

Any suitable $C_{1-26}$ alkyl may be substituted for $R^5$ and/or $R^6$, which may be the same or different. For example, $R^5$ and/or $R^6$ may be selected from, e.g., $C_{1-20}$ alkyl substituents, $C_{1-18}$ alkyl substituents, $C_{1-16}$ alkyl substituents, $C_{1-14}$ alkyl substituents, $C_{1-12}$ alkyl substituents, $C_{1-10}$ alky substituents 1, $C_{1-8}$ alkyl substituents, $C_{1-6}$ alkyl substituents, $C_{1-4}$ alkyl substituents, and the like. Suitable $C_{1-26}$ alkyl substituents, which may be substituted for $R^5$ and/or $R^6$, may include, for example, alkyl groups derived from readily available raw materials, e.g., methyl, ethyl, n-butyl, n-hexyl, n-octyl, n-decyl, n-dodecyl, n-tetradecyl, n-hexadecyl, n-octodecyl, and the like.

Variable a of formula (I) is preferably from 0-20, e.g., from 0-15, from 0-10, from 0-5, from 1-20, from 1-15, from 1-10, or from 1-5. Variable b of formula (I) is preferably from 0-20, e.g., from 0-15, from 0-10, from 0-5, from 1-20, from 1-15, from 1-10, or from 1-5. Variable c of formula (I) is preferably from 0-30, e.g., from 0-25, from 0-20, from 0-15, from 0-10, from 0-5, from 1-30, from 1-25, from 1-20, from 1-15, from 1-10, from 1-5, from 4-30, from 4-25, from 4-20, from 4-15, from 4-10, from 8-25, from 8-20, from 8-15, or from 8-10.

In one embodiment, a of formula (I) is at least 1 (e.g., from 1-20, from 1-15, from 1-10, or from 1-5). In one aspect of this embodiment, a of formula (I) is at least 1 (e.g., from 1-20, from 1-15, from 1-10, or from 1-5), and R5 and R6 are the same or different and each is C1-26 alkyl, e.g., methyl.

In another embodiment, a of formula (I) is at least 1 (e.g., from 1-20, from 1-15, from 1-10, or from 1-5), and b is at least 1 (e.g., from 1-20, from 1-15, from 1-10, or from 1-5). In one aspect of this embodiment, a of formula (I) is at least 1 (e.g., from 1-20, from 1-15, from 1-10, or from 1-5), b is at least 1 (e.g., from 1-20, from 1-15, from 1-10, or from 1-5), and $R^5$ and $R^6$ are the same or different and each is $C_{1-26}$ alkyl, e.g., methyl.

In another embodiment, a of formula (I) is at least 1 (e.g., from 1-20, from 1-15, from 1-10, or from 1-5), and c is at least 1 (e.g., from 1-30, from 1-25, from 1-20, from 1-15, from 1-10, from 1-5, from 4-30, from 4-25, from 4-20, from 4-15, from 4-10, from 8-25, from 8-20, from 8-15, or from 8-10). In one aspect of this embodiment, a of formula (I) is at least 1 (e.g., from 1-20, from 1-15, from 1-10, or from 1-5), c is at least 1 (e.g., from 1-30, from 1-25, from 1-20, from 1-15, from 1-10, from 1-5, from 4-30, from 4-25, from 4-20, from 4-15, from 4-10, from 8-25, from 8-20, from 8-15, or from 8-10), and R5 and R6 are the same or different and each is C1-26 alkyl, e.g., methyl.

In another embodiment, a of formula (I) is at least 1 (e.g., from 1-20, from 1-15, from 1-10, or from 1-5), b is 0, and c is at least 1 (e.g., from 1-30, from 1-25, from 1-20, from 1-15, from 1-10, from 1-5, from 4-30, from 4-25, from 4-20, from 4-15, from 4-10, from 8-25, from 8-20, from 8-15, from 8-10). In one aspect of this embodiment, a of formula (I) is at least 1 (e.g., from 1-20, from 1-15, from 1-10, or from 1-5), b is 0, c is at least 1 (e.g., from 1-30, from 1-25, from 1-20, from 1-15, from 1-10, from 1-5, from 4-30, from 4-25, from 4-20, from 4-15, from 4-10, from 8-25, from 8-20, from 8-15, or from 8-10), and $R^5$ and $R^6$ are the same or different and each is $C_{1-26}$ alkyl, e.g., methyl.

In another embodiment, a of formula (I) is at least 1 (e.g., from 1-20, from 1-15, from 1-10, or from 1-5), b is at least 1 (e.g., from 1-20, from 1-15, from 1-10, or from 1-5), and c is at least 1 (e.g., from 1-30, from 1-25, from 1-20, from 1-15, from 1-10, from 1-5, from 4-30, from 4-25, from 4-20, from 4-15, from 4-10, from 8-25, from 8-20, from 8-15, or from 8-10). In one aspect of this embodiment, a of formula (I) is at least 1 (e.g., from 1-20, from 1-15, from 1-10, or from 1-5), b is at least 1 (e.g., from 1-20, from 1-15, from 1-10, or from 1-5), c is at least 1 (e.g., from 1-30, from 1-25, from 1-20, from 1-15, from 1-10, from 1-5, from 4-30, from 4-25, from 4-20, from 4-15, from 4-10, from 8-25, from 8-20, from 8-15, or from 8-10), and R5 and R6 are the same or different and each is C1-26 alkyl, e.g., methyl.

In yet another embodiment, c of formula (I) is at least 1 (e.g., from 1-30, from 1-25, from 1-20, from 1-15, from 1-10, from 1-5, from 4-30, from 4-25, from 4-20, from 4-15, from 4-10, from 8-25, from 8-20, from 8-15, or from 8-10). In one aspect of this embodiment, c of formula (I) is at least 1 (e.g., from 1-30, from 1-25, from 1-20, from 1-15, from 1-10, from 1-5, from 4-30, from 4-25, from 4-20, from 4-15, from 4-10, from 8-25, from 8-20, from 8-15, or from 8-10), and at least one of $R^5$ and/or $R^6$ is of the formula:

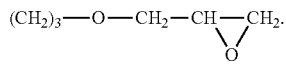

In one aspect of this embodiment, c of formula (I) is at least 1 (e.g., from 1-30, from 1-25, from 1-20, from 1-15, from 1-10, from 1-5, from 4-30, from 4-25, from 4-20, from 4-15, from 4-10, from 8-25, from 8-20, from 8-15, or from 8-10), at least one of $R^5$ and/or $R^6$ is of the formula:

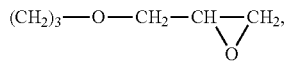

and a and b are 0. In another aspect of this embodiment, c of formula (I) is at least 1 (e.g., from 1-30, from 1-25, from 1-20, from 1-15, from 1-10, from 1-5, from 4-30, from 4-25, from 4-20, from 4-15, from 4-10, from 8-25, from 8-20, from 8-15, or from 8-10), $R^5$ and $R^6$ are of the formula:

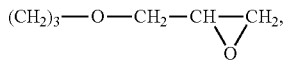

and a and b are 0.

In still yet another embodiment, a of formula (I) is from 1-15 (e.g., from 1-10, or from 1-5), b is from 0-15 (e.g., from 0-10, from 0-5, from 1-15, from 1-10, or from 1-5), and c is from 1-30 (e.g., from 1-25, from 1-20, from 1-15, from 1-10, from 1-5, from 4-30, from 4-25, from 4-20, from 4-15, from 4-10, from 8-25, from 8-20, from 8-15, or from 8-10). In one aspect of this embodiment, a of formula (I) is from 1-15 (e.g., from 1-10, or from 1-5), b is from 0-15 (e.g., from 0-10, from 0-5, from 1-15, from 1-10, or from 1-5), c is from 1-30 (e.g., from 1-25, from 1-20, from 1-15, from 1-10, from 1-5, from 4-30, from 4-25, from 4-20, from 4-15, from 4-10, from 8-25, from 8-20, from 8-15, or from 8-10), and $R^5$ and $R^6$ are the same or different and each is $C_{1-26}$ alkyl, e.g., methyl. In another aspect of this embodiment, a of formula (I) is from 1-15 (e.g., from 1-10, or from 1-5, b is from 0-15 (e.g., from 0-10, from 0-5, from 1-15, from 1-10, or from 1-5), and c is from 8-20 (e.g., 8, 10, or 20). In yet another aspect of this embodiment, a of formula (I) is from 1-15 (e.g., from 1-10, or from 1-5, b is from 0-15 (e.g., from 0-15, from 0-10, from 0-5, from 1-15, from 1-10, or from 1-5), c is from 8-20 (e.g., 8, 10, or 20), and $R^5$ and $R^6$ are the same or different and each is $C_{1-26}$ alkyl, e.g., methyl. In still yet another aspect of this embodiment, a of formula (I) is from 1-15 (e.g., from 1-10, or from 1-5), b is 0, and c is from 8-20 (e.g., 8, 10, or 20). In yet another aspect of this embodiment, a of formula (I) is from 1-15 (e.g., from 1-10, or from 1-5), b is 0, c is from 8-20 (e.g., 8, 10, or 20), and $R^5$ and $R^6$ are the same or different and each is $C_{1-26}$ alkyl, e.g., methyl.

A of formula (I) is preferably selected from one or more of $(CH_2—CH_2—O)_x$, $(CH(CH_3)—CH_2—O)_y$, and $(CH_2—CH(CH_3)—O)_z$, wherein x, y, and z are the same or different and each is preferably from 0-20, e.g., from 1-15, from 1-12, from 1-10, from 1-5, from 4-20, from 4-15, from 4-12, from 4-10, from 6-20, from 6-15, from 6-12, from 6-10, from 8-20, from 8-15, from 8-12, or from 8-10, provided that at least one of x, y, and/or z is at least 1. For example, any two of x, y, and z of formula (I) may be 0 and the other one may be from 1-20 (e.g., from 1-15, from 1-12, from 1-10, from 1-5, from 4-20, from 4-15, from 4-12, from 4-10, from 6-20, from 6-15, from 6-12, from 6-10, from 8-20, from 8-15, from 8-12, or from 8-10). Alternatively, any one of x, y, and z of formula (I) may be 0 and the other two may be from 1-20 (e.g., from 1-15, from 1-12, from 1-10, from 1-5, from 4-20, from 4-15, from 4-12, from 4-10, from 6-20, from 6-15, from 6-12, from 6-10, from 8-20, from 8-15, from 8-12, or from 8-10). Alternatively, all of x, y, and z of formula (I) may be from 1-20 (e.g., from 1-15, from 1-12, from 1-10, from 1-5, from 4-20, from 4-15, from 4-12, from 4-10, from 6-20, from 6-15, from 6-12, from 6-10, from 8-20, from 8-15, from 8-12, or from 8-10). Any variation of A can be combined with any of the other structural variations of formula (I) when b is at least 1.

In one embodiment, A of formula (I) is $(CH_2—CH_2—O)_x$, wherein x is from 1-20 (e.g., from 1-15, from 1-12, from 1-10, from 1-5, from 4-20, from 4-15, from 4-12, from 4-10, from 6-20, from 6-15, from 6-12, from 6-10, from 8-20, from 8-15, from 8-12, or from 8-10), and b is at least 1 (e.g., from 1-20, from 1-15, from 1-10, or from 1-5). In one aspect of this embodiment, A of formula (I) is $(CH_2—CH_2—O)_x$, wherein x is from 1-20 (e.g., from 1-15, from 1-12, from 1-10, from 1-5, from 4-20, from 4-15, from 4-12, from 4-10, from 6-20, from 6-15, from 6-12, from 6-10, from 8-20, from 8-15, from 8-12, or from 8-10), b is at least 1 (e.g., from 1-20, from 1-15, from 1-10, or from 1-5), and $R^5$ and $R^6$ are the same or different and each is $C_{1-26}$ alkyl, e.g., methyl. In another aspect of this embodiment, A of formula (I) is $(CH_2—CH_2—O)_x$, wherein x is from 1-20 (e.g., from 1-15, from 1-12, from 1-10, from 1-5, from 4-20, from 4-15, from 4-12, from 4-10, from 6-20, from 6-15, from 6-12, from 6-10, from 8-20, from 8-15, from 8-12, or from 8-10), b is at least 1 (e.g., from 1-20, from 1-15, from 1-10, or from 1-5), and c is at least 1 (e.g., from 1-30, from 1-25, from 1-20, from 1-15, from 1-10, from 1-5, from 4-30, from 4-25, from 4-20, from 4-15, or from 4-10). In yet another aspect of this embodiment, A of formula (I) is $(CH_2—CH_2—O)_x$, wherein x is from 1-20 (e.g., from 1-15, from 1-12, from 1-10, from 1-5, from 4-20, from 4-15, from 4-12, from 4-10, from 6-20, from 6-15, from 6-12, from 6-10, from 8-20, from 8-15, from 8-12, or from 8-10), b is at least 1 (e.g., from 1-20, from 1-15, from 1-10, or from 1-5), c is at least 1 (e.g., from 1-30, from 1-25, from 1-20, from 1-15, from 1-10, from 1-5, from 4-30, from 4-25, from 4-20, from 4-15, or from 4-10), and $R^5$ and $R^6$ are the same or different and each is 0126 alkyl, e.g., methyl. In still yet another embodiment, A of formula (I) is $(CH_2—CH_2—O)_x$, wherein x is from 1-20 (e.g., from 1-15, from 1-12, from 1-10, from 1-5, from 4-20, from 4-15, from 4-12, from 4-10, from 6-20, from 6-15, from 6-12, from 6-10, from 8-20, from 8-15, from 8-12, or from 8-10), a is at least 1 (e.g., from 1-20, from 1-15, from 1-10, or from 1-5), b is at least 1 (e.g., from 1-20, from 1-15, from 1-10, or from 1-5), and c is at least 1 (e.g., from 1-30, from 1-25, from 1-20, from 1-15, from 1-10, from 1-5, from 4-30, from 4-25, from 4-20, from 4-15, or from 4-10). In yet another embodiment, A of formula (I) is $(CH_2—CH_2—O)_x$, wherein x is from 1-20 (e.g., from 1-15, from 1-12, from 1-10, from 1-5, from 4-20, from 4-15, from 4-12, from 4-10, from 6-20, from 6-15, from 6-12, from 6-10, from 8-20, from 8-15, from 8-12, or from 8-10), a is at least 1 (e.g., from 1-20, from 1-15, from 1-10, or from 1-5), b is at least 1 (e.g., from 1-20, from 1-15, from 1-10, or from 1-5), c is at least 1 (e.g., from 1-30, from 1-25, from 1-20, from 1-15, from 1-10, from 1-5, from 4-30, from 4-25, from 4-20, from 4-15, or from 4-10), and $R^5$ and $R^6$ are the same or different and each is $C_{1-26}$ alkyl, e.g., methyl. In some embodiments, A of formula (I) is $(CH_2—CH_2—O)_x$, wherein x is from 4-12 (e.g., 4, 6, 8, 10, or 12).

Examples of representative compounds of formula (I) include the following:

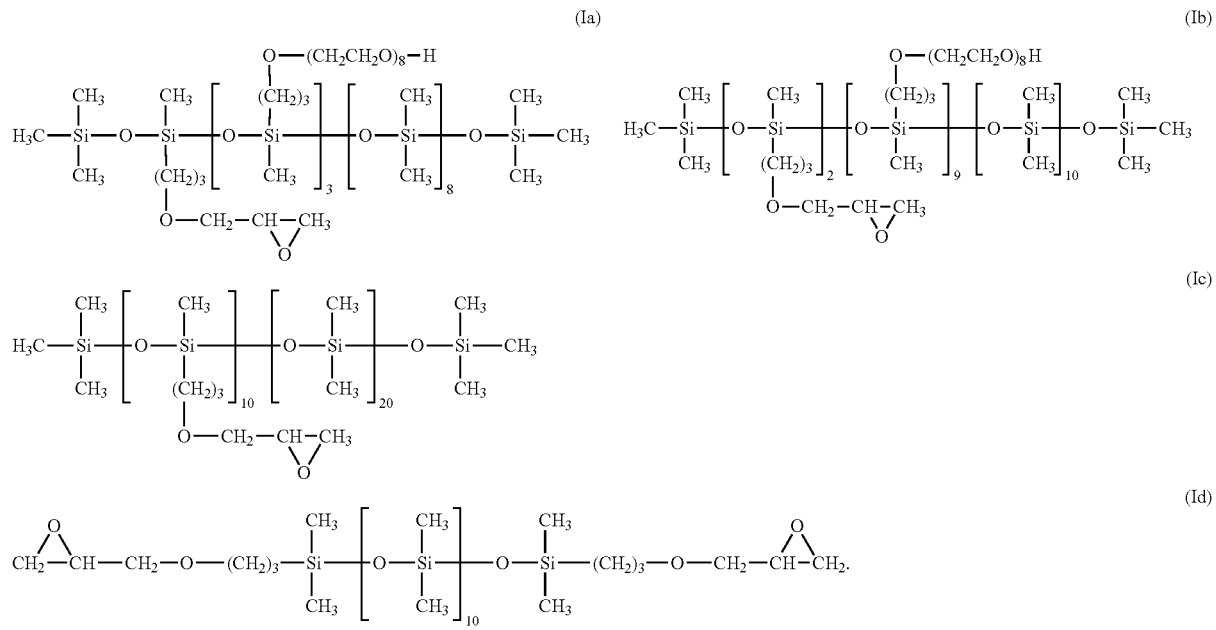

The compounds represented by formulae (Ia)-(Id) are currently sold by Siltech LLC of Lawrenceville, Ga. The compound represented by formula (Ia) is currently marketed by Siltech LLC under the trade name Silube® D208-1AGE or Silmer® D208-1AGE. The compound represented by formula (Ib) is currently marketed by Siltech LLC under the trade name Silube® J208-2AGE or Silmer® D208-1AGE. The compound represented by formula (Ic) is currently marketed by Siltech LLC under the trade name Silmer® EP J2. The compound represented by formula (Id) is currently marketed by Siltech LLC under the trade name Silmer® EP Di-10. The compounds represented by formula (Ic) and (Id) are preferably formulated as aqueous emulsions.

The method of the present invention includes treating hair damage caused by exposure to natural and/or unnatural conditions that can damage hair. Such conditions may include, for example, chemical damage, sunlight, air oxidation, mechanical stress, and the like, or any combination thereof. The method of the present invention includes prophylactically and/or therapeutically treating hair damage associated with exposure to such conditions. The method of the present invention accordingly may be used for protecting hair from damage, e.g., reducing the likelihood, extent, degree, or severity of damage associated with exposure to damaging conditions, and/or for repairing damaged hair, e.g., improving the structural integrity of, strengthening, improving the elasticity of, and/or mending hair damaged associated with exposure to such conditions. Without wishing to be bound by any particular theory, it is believed that the compound of formula (I) may react with damaged regions of the hair in which disulfide (—S—S—) bonds have been broken from exposure to damaging conditions. Again without wishing to be bound by any particular theory, it is believed that the compound of formula (I) may act as a cross-linking agent in such damaged regions, thereby strengthening hair fibers in terms of elasticity, e.g., by restoring structural integrity within damaged regions. The method of the present invention has been found to be particularly useful in treating hair damage associated with conditions that cause disulfide bond breakage (e.g., hair lightening/bleaching, hair relaxing, and oxidative hair dyeing, permanent waving with reducing agents, and modifying cysteine bonds with aldehydic compounds).

In accordance with the method of the present invention, the hair is contacted with an effective amount of at least one compound of formula (I) as described herein. An effective amount is preferably an amount that is effective for treating hair damage associated with exposure to conditions that are damaging to hair fibers, e.g., exposure to conditions that cause disulfide bond breakage. Preferably, the effective amount is effective for reducing the likelihood, extent, degree, or severity of damage associated with exposure to such conditions, and/or is effective for repairing damaged hair, e.g., improving the structural integrity of, strengthening, improving the elasticity of, and/or mending hair damaged by exposure to such conditions.

The method of the present invention may be used for treating hair damage caused by a hair altering process that is capable of damaging hair fibers. Examples of hair altering processes that are capable of damaging hair fibers include cosmetic processes that utilize oxidants and/or strongly alkaline reagents, which are damaging to hair. Such procedures can include, for example, hair lightening/bleaching procedures, hair relaxing procedures, hair dyeing procedures, permanent waiving, smoothing, and the like.

In one embodiment, the method of the present invention includes treating hair damage associated with application of an oxidative hair lightening/bleaching agent to the hair, by contacting the hair with an effective amount of at least one compound of formula (I) as described herein. In this embodiment, an effective amount of the compound of formula (I) may be applied to the hair before, concurrently, or following application of the oxidative hair lightening/bleaching agent to the hair. Advantageously, the compound of formula (I) and the oxidative hair lightening/bleaching agent may be combined together, to form a hair lightening/ bleaching composition containing an effective amount of the compound of formula (I), before application to the hair. When the compound of formula (I) and oxidative hair lightening/bleaching agent are so combined, the concentration of the compound of formula (I) in the resulting composition is preferably from about 0.1 wt % to about 10 wt %, e.g., from about 0.5 wt % to about 10 wt %, from about 1 wt % to about 10 wt %, from about 1 wt % to about 9 wt %, from about 1 wt % to about 5 wt %, or from about 1 wt % to about 2 wt %. Suitable hair lightening/bleaching agents can include, for example, mixtures prepared by combining at least one persulfate and at least one peroxide. Suitable persulfates can include, for example, potassium persulfate, ammonium persulfate, and combinations thereof. Suitable peroxides can include, for example, hydrogen peroxide.

In another embodiment, the method of the present invention includes treating hair damage associated with application of a hair relaxing agent to the hair, by contacting the hair with an effective amount of at least one compound of formula (I) as described herein. In this embodiment, an effective amount of the compound of formula (I) may be applied to the hair before, concurrently, or following application of the hair relaxing agent to the hair. Advantageously, the compound of formula (I) and the hair relaxing agent may be combined together, to form a hair relaxing composition containing an effective amount of the compound of formula (I), before application to the hair. When the compound of formula (I) and hair relaxing agent are so combined, the concentration of the compound of formula (I) in the resulting composition is preferably from about 0.1 wt % to about 10 wt %, e.g., from about 0.5 wt % to about 10 wt %, from about 1 wt % to about 10 wt %, from about 1 wt % to about 9 wt %, from about 1 wt % to about 5 wt %, or from about 1 wt % to about 2 wt %. Suitable hair relaxing agents can include, for example, mixtures prepared by combining at least one metal hydroxide and at least one alkaline salt of guanidine. Metal hydroxides suitable for relaxer systems can include, for example, calcium hydroxide. Alkaline salts of guanidine suitable for relaxer systems can include, for example, guanidine carbonate.

In yet another embodiment, the method of the present invention includes treating hair damage associated with application of an oxidative hair dyeing agent, by contacting the hair with an effective amount of at least one compound of formula (I) as described herein. In this embodiment, an effective amount of the compound of formula (I) may be applied to the hair before, concurrently, or following application of the oxidative hair dyeing agent to the hair. Advantageously, the compound of formula (I) and oxidative hair dyeing agent may be combined together, to form a oxidative hair dyeing composition containing an effective amount of the compound of formula (I), before application to the hair. When the compound of formula (I) and oxidative hair dyeing agent are so combined, the concentration of the compound of formula (I) in the resulting composition is preferably from about 0.1 wt % to about 10 wt %, e.g., from about 0.5 wt % to about 10 wt %, from about 1 wt % to about 10 wt %, from about 1 wt % to about 9 wt %, from about 1 wt % to about 5 wt %, or from about 1 wt % to about 2 wt %. Suitable oxidative hair dyeing agents can include, for example, mixtures prepared by combining at least one permanent hair dyeing agent with at least one peroxide. In some embodiments, the permanent hair dyeing agent includes two or more permanent hair dyes. Peroxides suitable for use in oxidative hair dyeing systems include hydrogen peroxide.

The present invention additionally provides a composition comprising a carrier and a hair damage treating effective amount of at least one compound of formula (I) as described herein. The composition of the present invention may further include a hair altering agent that is capable of damaging hair fibers. Such hair altering agents can include, for example, oxidative hair lightening/bleaching agents, hair relaxing agents, oxidative hair dyeing agents, permanent waving agents, and smoothing agents, as described herein. In one embodiment, the carrier used in the composition of the present invention is a liquid vehicle. Preferably, the liquid vehicle is an aqueous liquid vehicle such as, for example, water, water containing one or more aqueous co-solvents, water containing one or more aqueous solutes, and the like, and combinations thereof. The water solubility of the compound of formula (I) may potentially impact how one of ordinary skill in the art might approach formulating the compound in an aqueous liquid vehicle. If desired, the alkylene oxide containing siloxane subunit(s) represented the formula:

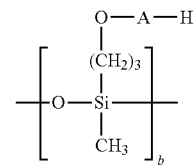

may be incorporated within the structure in an appropriate ratio to impart, improve and/or attain a desired degree of water solubility. However, the compound of formula (I) need not be water soluble in order to be formulated in an aqueous vehicle, and need not be water soluble in order to be effective for purposes of treating hair damage. As such, the compound of formula (I) may be water soluble, sparingly soluble in water, or water insoluble and still be effective for purposes of the present invention.

When the compound of formula (I) is water soluble, the composition of the present invention may be formulated as an aqueous solution. An example of a compound of formula (I), which is sufficiently soluble to be formulated as an aqueous solution is Silube® D208-1AGE or Silmer® D208-1AGE (formula (Ia), Siltech LLC). When the compound of formula (I) is insoluble (or only sparingly soluble) in water, the compound of formula (I) is preferably formulated as an aqueous emulsion. Water insoluble compounds of formula (I) may be formulated as aqueous emulsions by any suitable method, including methods that are known in the art for formulating aqueous emulsions of water insoluble organic compounds. Suitable emulsions may include one or more emulsifiers, which are effective in stabilizing aqueous emulsions of the compound of formula (I). Suitable emulsifiers may include, for example, emulsifying phosphate esters, e.g., dicetyl phosphate and ceteth-10 phosphate, polyoxyalkylene sorbitan esters, e.g., polysorbates, e.g., polysorbate 20, polysorbate 40, polysorbate 60, and the like, and combinations thereof. When the compound of formula (I) is formulated as an emulsion, the emulsion preferably includes from about 2 wt % to about 75 wt % of the compound of formula (I), e.g., from about 5 wt % to about 50 wt % of the compound of formula (I), e.g., from about 10 wt % to about 30 wt % of the compound of formula (I). In one embodiment, the composition of the present invention is formulated as an aqueous emulsion containing about 10-30 wt % (e.g., about 25 wt %) of the compound of formula (I). In one aspect of this embodiment, the composition of the present invention is preferably formulated as an aqueous emulsion containing up to about 25 wt % of the compound of formula (Ic) (Silmer® EP J2, Siltech LLC). In another aspect of this embodiment, the compound of the present invention is preferably formulated as an aqueous emulsion containing up to about 20 wt % of the compound of formula (Id) (Silmer® EP Di-10, Siltech LLC). The emulsions of the present invention are preferably formulated as micro-emulsions or nano-emulsions. Such emulsions may be prepared by a microfluidization process using, for example, using a Microfluidics Microfluidizer® Processor, Model #110Y (High Pressure Pneumatic), with a collision/interaction chamber consisting of Z configuration at a pressure of 2500-23,000 psi (e.g., 14,000 psi). The resulting emulsion preferably has a particle size of from about 100 nm to about 250 nm.

The present invention further provides a product, which includes a hair damage treating effective amount of at least one compound of formula (I) as described herein, and instructions for applying the compound of formula (I) to the hair. If desired, the compound of formula (I) may be formulated as a composition, e.g., in combination with a carrier, as described herein. The carrier may include a liquid vehicle such as, for example, an aqueous liquid vehicle, as described herein. The compound of formula (I) may be formulated as an aqueous solution or aqueous emulsion as described herein.

The product of the present invention may further include a hair altering agent, combined with or contained separately from the compound of formula (I), and instructions for applying the hair altering agent to the hair. The hair altering agent may include one or more hair altering agents that are capable of damaging hair fibers. Suitable hair altering agents capable of damaging hair fibers may include, for example, oxidative hair lightening agents, hair relaxing agents, and oxidative hair dyeing agents, as described herein. When the product of the present invention further includes a hair altering agent, the instructions, e.g., the instructions for applying the compound of formula (I), instructions for applying the hair altering agent, or both, may include instructions for applying the compound of formula (I) before, concurrently, or following application of the hair altering agent to the hair. In one embodiment, the product of the present invention further includes a hair altering agent and instructions for combining the hair altering agent and the compound of formula (I) before application to the hair. When the compound of formula (I) is soluble in water, the compound of formula (I) in the product of the invention may be formulated as an aqueous solution as described herein. When the compound of formula (I) is insoluble in water, the compound of formula (I) in the product of the invention may be formulated as an aqueous emulsion as described herein.

The compound of formula (I) may be combined or used in conjunction with one or more catalysts, which are preferably capable of augmenting epoxide reactivity. One or more of such catalysts may be included in or used in conjunction with the compositions and products of the present invention. The catalyst may include one or more metal catalysts such as, e.g., zirconium catalysts, titanium catalysts, and the like, and combinations thereof. Suitable catalysts may include, for example, zirconium oxides (e.g., zirconium dioxide) and titanium oxides (e.g., titanium dioxide).

The following examples further illustrate the invention, but should not be construed as in any way limiting its scope.

Analytical Methods

ISR Test: Human hair consists of two mechanically distinct phases, the elastic microfibrils, also called the intermediate filaments (IFs) and a hydrophilic, viscous matrix. These two phases respond in different ways to deformational forces applied during the mechanical testing. If the force is applied instantly and for a short time, the hair behaves like an elastic, solid material because there is no time for the matrix proteins to undergo a flow process and relax the imposed stress.

The intermittent stress relaxation ("ISR") test probes the hair with a short pulse of force, which is followed by a longer time of relaxation during which the hair is not subjected to any tension. The force is programmed in such a manner that the instrument extends the hair for 0.10 minute to 0.5% strain and measures the maximum stress generated inside it. Subsequently, the force is dropped to zero and the hair is allowed to relax for the next 0.90 minute. The cycle is repeated ten times. Since the measurement is done for the same section of the same hair fiber twice, before and after the chemical treatment, the changes in stress reflect damage to the elastic strength of hair inflicted, e.g., by mechanical stress and/or other types of stresses such as, e.g., chemical damage. The relative strength of, for example, chemically treated hair, may be measured a posteriori after finalizing of the chemical process.

In some studies, the ISR test is conducted twice on the same hair fiber immersed in water, once before the chemical treatment, and subsequently after the treatment. The stress measured at 0.5% strain is compared and its drop after the chemical treatment is used as a measure of fiber strength after chemical treatment.

The intermittent stress relaxation (ISR) test is used to assess the internal chemical damage of hair via loss in elastic strength of wet hair fibers using the TA's Dynamic Mechanical Analyzer model Q800. The instrument consists of a drive motor that provides the static and dynamic or oscillatory force. The drive motor transmits force directly to the rectangular air-bearing slide that is also connected to the drive shaft and sample clamp. The compressed air supplied to the air bearings allows the slide to float. The distance or vertical movement of the air-bearing slide during testing is translated to the force required for that specific run. The optical encoder is used to measure the displacement during testing based on diffraction patterns of light through gratings (one stationary and one moveable). The furnace provides temperature control required during testing.

In this test, each single fiber (gauge length=14.82 mm) is mounted to the submersible fiber specimen clamp containing water. The fiber is stretched to a constant strain or 0.5% of its length (from 14.82 to 14.894 mm length) for 0.1 minute and allowed to recover for 0.90 minute. This process of imposing the strain and allowing it to recover is repeated for a total of 10 cycles. The force is expressed in grams while the area is expressed in denier (a textile terminology defined as weight in grams of 9,000 meters of yarns or fibers). The area of the hair specimen is measured using the LaserMike® scanning micrometer. The average area is recorded as (x+y)/2 where x is the minor axis and y the major axis. The amount of stress (g/denier) for each cycle is measured and recorded. If desired, the results may be depicted as an intermittent stress curve. The ratio of after-to-before treatment force is calculated and used to assess the internal condition of hair fibers. An index of 1.0 indicates that there is no chemical damage done to the hair, while a value less than 1.0 indicates that the fibers are internally damaged by the treatment.

One advantage of this method over the conventional tensile strength test (fiber stretched to the breakpoint) is that the ISR test is performed within the Hookean region (<2% strain), i.e., a fiber is stretched to a constant elongation of 0.5% strain. At this specified elongation, it is demonstrated that a chemically untreated hair could be repeatedly stretched without undergoing permanent physical deformation. Measuring the elastic strength of wet hair in the range of 0.5 to about 1% strain is believed to simulate the range of strain applied during a conventional grooming process, such as combing, brushing, styling and setting of the hair.

Combing/Brushing Damage Testing: In order to mimic real life hair fatigue associated with combing and brushing, a combing/brushing device may be constructed in order to brush hair tresses repeatedly for up to 3600 times. The fibers broken upon brushing may be counted in order to ascertain the extent of damage upon repeated brushing of hair. This allows comparisons to be made between various treatments with control versus products containing damage reducing ingredients.

The combing/brushing machine can include an arm, which is capable of revolving in circular motion. This arm may be equipped with a brush or comb of choice, and in its path a stationary hair tress may be attached to another arm. This allows tresses to be combed or brushed at a specific speed, e.g., with the help of a motorized arm to which a selected comb or brush is attached.

The test may be carried out using a combing/brushing device as shown in FIG. 1. The device depicted in FIG. 1 includes a brush, a digital counter (which counts the number of brushing strokes), a motor with an attached cylindrical bar from which two circular metal plates are mounted to hold the brush/comb, a tress holder, and black/white plastic sheets to collect broken fibers. The brushing speed can be set at the rate of 52 strokes per minute, which represents the median brushing strokes for twenty (20) women of varying ages and ethnicities based on salon testing. Advantageously, all hair tresses, treated and untreated, may be brushed multiple times for a total of 10,000 brushing strokes. Four (4) hair tresses may be used for each group. Desirably, broken hair fibers are counted after every 400 strokes up until the completion of, e.g., 10,000 brushing strokes. The number of broken fibers may be collected and recorded, e.g., in a spreadsheet. This test is preferably performed in a humidity controlled room, e.g., where the relative humidity is set at 45%. Literature relating to this topic includes Dubief, et al., Hair Care Products in *The Science of Hair Care*. Ed: Claude Nouillon and John Wilkinson, Taylor & Francis, Boca Raton, Fla., p. 144 (2005); Leroy, F., Flexabrasion: A new test for predicting human hair resistance, Conference at the First Tri-Continantal Symposium, Bruxelles, Belgium (1995); Evans, T., Hair breakage. In *Practicle Modern Hair Science*. Ed. Evans & Wickett. Allured: Carol Stream, Ill., p. 281 (2012); and Evans, et al., *J Cosmet Sci*, 61, 439-455 (2010).

Figure 2:
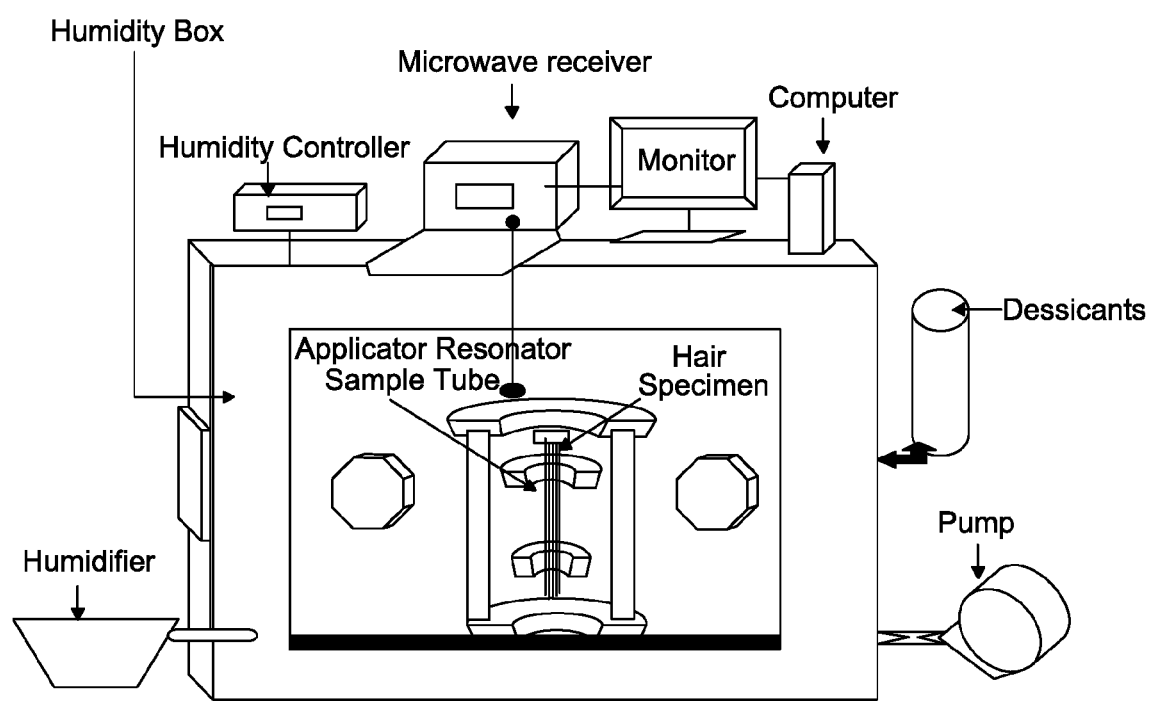
FIG. 2 depicts a device for determining the moisture content of hair fibers using microwave resonance.

Moisture Content Testing: The moisture content of hair fibers may be tested using a microwave resonance device, which takes advantage of the fact that water molecules are very small and movable. They possess a strong electrical dipole field that can exhibit a measurable effect to an external electrical measuring field. The test is preferably performed inside a controlled humidity box model 506A from ETS (Electro Tech Systems, Inc.) equipped with a pump, desiccants, dehumidification system, circulating fan, humidity control sensor and humidity controller as shown in FIG. 2. The microwave moisture measuring system used in this test may include an applicator resonator chamber and microwave generator/receiver. In FIG. 2, the resonator (MW 3150 Moisture Wave Device) is coupled with an 18 mm sensor chamber from TEWS Electronik, Germany. Microwaves resonate in an empty chamber. Inserting each hair specimen onto the applicator tube shifts the resonance down and increases the bandwidth that enables measurement of the microwave resonance values. The resonance values are calibrated against the moisture content of hair sample obtained via gravimetric analysis from humidity range of 35% to 80% RH, thus enabling recordation of the relative moisture content of hair directly from the resonator. The test is considered non-destructive, and the sample is covered by the electrical field. The system measures the total amount of moisture contained in the sample volume (free bound and tightly bound moisture). Literature relating to this topic can be found in TEWS EleKtronik Technical Manual for Innovative Microwave Resonance Technology Process and Laboratory for Measuring Moisture Content.

Example 1

This example demonstrates compositions of the present invention and methods of using them for treating hair damage associated with a hair lightening process.

Tables 1A-1C below describe a conventional lightening powder, a conventional hydrogen peroxide developer, and a conventional non-conditioning shampoo, respectively.

TABLE 1A

Conventional powder lightener

| Ingredient | Weight Percent |
|---|---|
| Potassium Persulfate | 49.1 |
| Ammonium Persulfate | 15.3 |
| Sodium Metasilicate | 16.5 |
| Hydroxyethylcellulose | 4.9 |
| Magnesium Carbonate | 5.5 |
| Silica | 1.0 |
| Sodium Lauryl Sulfate | 1.0 |
| Tetrasodium EDTA | 0.5 |
| Ultramarines | 0.2 |
| Ethylhexyl Pelargonate | 3.0 |
| *Helianthus Annuus* (Sunflower) Seed Oil | 3.0 |

TABLE 1B

Conventional hydrogen peroxide developer 40 volume

| Ingredient | Weight Percent |
|---|---|
| Water | 67.6400 |
| Etidronic Acid (60%) | 0.1000 |
| Sodium Stannate | 0.1000 |
| Lipocol-C (Cetyl Alcohol) | 3.5000 |
| Procol CA - 10 | 1.5000 |
| Anti Foam A Compound | 0.0500 |
| Carsoquat CT-429 | 2.5000 |
| Aculyn 46 Polymer | 0.2100 |
| Hydrogen Peroxide 50% (FMC) | 24.0000 |
| Phosphoric Acid (85%) | 0.2000 |
| Sodium Dihydrogen Phosphate | 0.2000 | pH = 3.51,
Viscosity = 3,000 cps

TABLE 1C

Conventional non-conditioning shampoo

| Ingredient | Weight Percent |
|---|---|
| Water | 64.7975 |
| Disodium EDTA | 0.20 |

TABLE 1C-continued

Conventional non-conditioning shampoo

| Ingredient | Weight Percent |
|---|---|
| Ammonium Lauryl Sulfate (30.0% Active) | 30.00 |
| Mackamide BY-23 | 4.50 |
| Citric Acid | 0.45 |
| Phenol Red | 0.0025 |
| Kathon CG | 0.05 | pH = 4.51;
Viscosity = 1700 cps

A group of control hair fibers was treated with conventional powder lightener of Table 1A and a conventional 40-volume developer of Table 1B. The mixing ratio of the hydrogen peroxide Developer and the powder lightener was 2:1. The application procedure was as follows:

1. The untreated hair specimens were pre-tested on DMA using the intermittent stress relaxation test.
2. The pre-tested hair fibers (Caucasian, IMHAIR) were embedded on a 4 g of hair tress.
3. 32 g of a mixture prepared by combining 1 part (30 g) of control conventional bleaching powder (Table 1A) and 2 parts (60.0 g) of the control 40 volume developer (Table 1B) was applied for 50 minutes. The hair tress was not wrapped in aluminum foil. The ratio of hair tress to bleaching mixture applied was 1:8.
4. The hair was rinsed with water for 3 minutes.
5. 5 g of non-conditioning shampoo (Table 1C) was applied for 3 minutes, the hair fibers were rinsed for 3 minutes, and air-dried.
6. The stress at 0.50% strain as in step 1 and the ratio of the stress (force) were determined before and after treatment, to determine the ISR.

The ISR test results for the control fibers are summarized below in Table 1D.

TABLE 1D

ISR data for hair fibers treated with conventional lightener

| Fiber | Strength Before Treatment | Strength After Treatment | Intermittent Stress Relaxation (ISR) |
|---|---|---|---|
| 1 | 52.20 | 45.52 | 0.87 |
| 2 | 50.63 | 43.31 | 0.85 |
| 3 | 46.58 | 41.13 | 0.88 |
| 4 | 58.30 | 52.82 | 0.91 |
| 5 | 50.24 | 41.86 | 0.83 |
| 6 | 46.60 | 38.21 | 0.82 |
| 7 | 38.23 | 33.02 | 0.86 |
| 8 | 46.89 | 39.00 | 0.83 |
| 9 | 43.81 | 39.42 | 0.90 |
| 10 | 57.73 | 61.14 | 0.94 |
| 11 | 47.76 | 38.88 | 0.81 |
| 12 | 41.55 | 40.58 | 0.98 |
| Average | 48.38 | 42.91 | 0.87 |
| Standard Deviation | 5.94 | 7.45 | 0.05 |
| Coefficient of Variation | 12.28 | 17.37 | 5.73 |

Table 1E below describes compositions containing an epoxysilicone of formula (I) (sometimes referred to as "bond regenerator") for treating hair damage.

TABLE 1E

Aqueous epoxysilicone compositions

| | Wt % | |
|---|---|---|
| Ingredient | Formulation 1E-1 | Formulation 1E-2 |
| Deionized Water | 25 | 75 |
| Silube D208-1AGE (Siltech LLC, lot # 019118) | 75 | 25 |

For the epoxysilicone treated hair fibers, 60 g of Conventional 40 Volume developer (Table 1B) and 30 g of Conventional Powder Lightener (Table 1A) were placed in a bowl, and 7.5 g of bond multiplier (Table 1E, Formulation 1E-1 or 1E-2) was added. This mixture was stirred well using an applicator brush until the mixture became smooth. The application procedure was as follows:

1. The untreated hair specimens were pre-tested on DMA using the intermittent stress relaxation test.
2. The pre-tested hair fibers (Caucasian, IMHAIR) were embedded on a 4 g of hair tress.
3. 32 g of a mixture prepared by combining 30 g (1 part) of control conventional bleaching powder (Table 1A) and 60 g (2 parts) of the control developer 40 Volume (Table 1B) and 7.5 g of bond multiplier (Table 1E, Formulation 1E-1 or 1E-2), was applied for 45 minutes. The hair tress was not wrapped in aluminum foil. The ratio of hair tress to bleaching mixture applied was 1:8.
4. The hair was rinsed with water for 3 minutes.
5. 5 g of non-conditioning shampoo (Table 1C) was applied for 3 minutes, the hair was rinsed for 3 minutes, and air-dried.
6. The stress for 0.50% strain as in step 1 and the ratio of the stress (force) were determined before and after treatment to determine the ISR.

The ingredients used in the lightening composition containing epoxysilicone are summarized below in Table 1F.

TABLE 1F

Depiction of the ratios used in lightening composition containing expoxysilicone

| Ingredients | Ratio | Wt % |
|---|---|---|
| Conventional Powder Lightener (Table 1A) | 30 | 30.77 |
| Conventional 40 Vol Developer (Table 1B) | 60 | 61.54 |
| Bond Regenerator (Table 1E, Formulation 1E-1) | 7.5 | 7.69 (5.77 wt % active) |

The test results for the hair fibers treated with lightening composition containing epoxysilicone (Table 1F) are summarized below in Table 1G.

TABLE 1G

ISR data for fibers treated with conventional lightening composition containing Silube D 208-1AGE (5.77 wt % active)

| Fiber | Un-Treated | Treated | ISR |
|---|---|---|---|
| 1 | 44.64 | 47.55 | 1.07 |
| 2 | 57.35 | 51.80 | 0.90 |
| 3 | 49.92 | 55.41 | 1.11 |
| 4 | 67.36 | 55.73 | 0.83 |
| 5 | 54.67 | 50.85 | 0.93 |
| 6 | 49.47 | 52.11 | 1.05 |
| 7 | 55.27 | 59.28 | 1.07 |
| 8 | 45.70 | 41.53 | 0.91 |

TABLE 1G-continued

ISR data for fibers treated with conventional lightening composition containing Silube D 208-1AGE (5.77 wt % active)

| Fiber | Un-Treated | Treated | ISR |
|---|---|---|---|
| 9 | 32.69 | 36.68 | 1.12 |
| 10 | 65.61 | 62.39 | 0.95 |
| 11 | 64.10 | 58.88 | 0.92 |
| 12 | 70.51 | 66.91 | 0.95 |
| Average | 54.78 | 53.26 | 0.98 |
| SD | 10.24 | 7.80 | 0.10 |
| Coefficient of Variance | 18.70 | 14.65 | 10.39 |

The ingredients used in another lightening composition containing epoxysilicone are summarized below in Table 1H.

TABLE 1H

Depiction of ratios in lightening composition containing epoxysilicone

| Ingredients | Ratio | Wt % |
|---|---|---|
| Conventional Powder Lightener (Table 1A) | 30 | 30.77 |
| Conventional 40 Vol Developer (Table 1B) | 60 | 61.54 |
| Bond Multiplier (Table 1E, Formulation 1E-2) | 7.5 | 7.69 (1.92 wt % active) |

The test results for the hair fibers treated with lightening composition containing Silube D208-1AGE (Table 1H) are summarized below in Table 1I.

TABLE 1I

ISR data for fibers treated with conventional developer and powder lightener containing Silube D 208-1AGE (1.92 wt % Active)

| Fiber | Un-Treated | Treated | ISR |
|---|---|---|---|
| 1 | 71.38 | 61.79 | 0.87 |
| 2 | 56.59 | 61.58 | 1.09 |
| 3 | 52.26 | 54.13 | 1.04 |
| 4 | 54.79 | 44.94 | 0.82 |
| 5 | 39.21 | 41.21 | 1.05 |
| 6 | 49.75 | 52.77 | 1.06 |
| 7 | 51.77 | 55.16 | 1.07 |
| 8 | 57.61 | 44.52 | 0.77 |
| 9 | 59.40 | 56.26 | 0.95 |
| 10 | 31.65 | 27.95 | 0.88 |
| 11 | 64.93 | 57.29 | 0.88 |
| 12 | 55.30 | 58.26 | 1.05 |
| Average | 53.72 | 51.32 | 0.96 |
| SD | 10.51 | 9.92 | 0.11 |
| CV | 19.57 | 19.34 | 11.59 |

The epoxysilicone treated hair fibers exhibited significantly greater strength relative to control, demonstrating a significant reduction in damage associated with a conventional hair lightening process.

Example 2

This example demonstrates compositions of the present invention and methods of using them for treating hair damage associated with a hair relaxing process.

Tables 2A-2C describe a conventional sensitive scalp relaxer, a conventional liquid activator, and a conventional neutralizing shampoo, respectively.

TABLE 2A

Conventional sensitive scalp relaxer

| Ingredient Name | Wt % |
|---|---|
| Petrolatum | 23.00 |
| Mineral Oil | 13.50 |
| Polawax (Emulsifying Wax NF) | 11.00 |
| Polychol 15 | 1.00 |
| Super Solan | 0.50 |
| Water | 33.50 |
| Propylene Glycol | 2.00 |
| Calcium Hydroxide | 5.50 | pH = 12.5,
Viscosity = 52,000 cps

TABLE 2B

Conventional liquid activator

| Ingredient Name | Wt % |
|---|---|
| DEIONIZED WATER | 72.34940 |
| KELTROL CG | 0.25000 |
| DISSOLVINE Na2-S | 0.20000 |
| GUANIDINE CARBONATE | 27.20000 |
| FD&C RED #40 POWDER | 0.00060 | pH = 11.26;
Viscosity = 780 cps

TABLE 2C

Conventional neutralizing shampoo

| Ingredient | Wt % |
|---|---|
| Water | 84.7975 |
| Disodium EDTA | 0.20 |
| Ammonium LaurylSulfate | 10.00 |
| Mackamide BY-23 | 4.50 |
| Citric Acid | 0.45 |
| Phenol Red | 0.0025 |
| Kathon CG | 0.05 | pH = 4.51;
Viscosity = 1700 cps

A group of control hair fibers was treated with a non-conditioning formula of guanidine hydroxide relaxer, non-conditioning liquid activator and non-conditioning neutralizing shampoo shown in Tables 2A-2C, respectively. The ratio of relaxer cream to liquid activator was 3.78:1, and the relative concentrations are shown below in Table 2D.

TABLE 2D

Depiction of ratios used in conventional relaxer composition

| Components | Wt % |
|---|---|
| Non-conditioning Calcium Hydroxide Cream (Table 2A) | 79.10 |
| Non-Conditioning Liquid Activator (Table 2B) | 20.90 |

The treatment procedure for the control group was as follows. On each 2 g of hair tress, 8.0 g mixture of Non-conditioning Sensitive Scalp cream relaxer (Table 2A) plus Affirm Liquid Activator (Table 2B) was prepared as shown in Table 2D, and the mixture was applied. The relaxer cream mixture was left on the hair for 18 minutes. The treated fibers were rinsed after 18 minutes and shampooed twice with Non-Conditioning Neutralizing Shampoo (Table 2C). The fibers were then rested overnight and the ISR was determined for the fibers.

The ISR data at 100% RH for the control group of fibers is summarized below in Table 2E.

TABLE 2E

ISR data at 100% humidity for control fibers treated with conventional guanidine hydroxide relaxer (wet fibers)

| Fiber | Strength Before Treatment | Strength After Treatment | Intermittent Stress Relaxation |
|---|---|---|---|
| 1 | 12.39 | 7.03 | 0.57 |
| 2 | 14.1 | 5.43 | 0.39 |
| 3 | 11.98 | 3.17 | 0.26 |
| 4 | 11.9 | 5.47 | 0.46 |
| 5 | 10.82 | 4.51 | 0.42 |
| 6 | 13.4 | 4.72 | 0.35 |
| 7 | 13.81 | 4.16 | 0.30 |
| 8 | 12.97 | 6.43 | 0.50 |
| 9 | 15.42 | 5.17 | 0.34 |
| 10 | 12.85 | 5.1 | 0.40 |
| Average | 12.96 | 5.12 | 0.40 |
| Standard Deviation | 1.30 | 1.10 | 0.09 |
| Coefficient of Variation | 10.05 | 21.44 | 23.44 |

The average elasticity of the relaxer treated fibers was approximately 40% and the loss of elasticity was approximately 60% following the relaxing process. Such a loss of elasticity could be devastating for the integrity of hair survival under normal grooming conditions such as combing and brushing.

The epoxysilicone treated hair fibers were subjected to the same relaxing process that was used for the control fibers, except that Silube D 208-1 AGE was added to the relaxer system as shown below in Table 2F.

TABLE 2F

Guanidine hydroxide relaxer containing epoxysilicone

| Components | Wt % |
|---|---|
| Non-conditioning Calcium Hydroxide Cream (Table 2A) | 76.10 |
| Non-Conditioning Liquid Activator (Table 2B) | 20.90 |
| Silube D 208-1 AGE (100.00% Active) | 3.00 |

The ISR data at 100% RH for the hair fibers treated with the relaxer system containing epoxysilicone (Table 2F) is summarized below in Table 2G.

TABLE 2G

ISR data at 100% humidity for fibers treated with guanidine hydroxide relaxer containing 3.0 wt % Silube D 208-1 AGE (wet fibers)

| Fiber | Strength Before Treatment | Strength After Treatment | Intermittent Stress Relaxation |
|---|---|---|---|
| 1 | 52.33 | 41.30 | 0.79 |
| 2 | 56.15 | 41.79 | 0.74 |
| 3 | 47.19 | 31.46 | 0.67 |
| 4 | 59.14 | 34.07 | 0.58 |
| 5 | 55.33 | 37.76 | 0.68 |
| 6 | 63.69 | 40.01 | 0.63 |
| 7 | 55.64 | 37.73 | 0.68 |
| 8 | 59.58 | 34.60 | 0.58 |
| 9 | 67.35 | 36.51 | 0.54 |
| 10 | 43.24 | 31.90 | 0.74 |
| 11 | 66.42 | 34.83 | 0.79 |
| 12 | 62.79 | 35.93 | 0.57 |
| Average | 57.40 | 36.49 | 0.67 |
| Standard Deviation | 7.36 | 3.38 | 0.09 |
| Coefficient of Variance | 12.83 | 9.27 | 13.19 |

The epoxysilicone treated hair fibers exhibited significantly greater strength relative to control, demonstrating a significant reduction in damage associated with a conventional hair relaxing process. The fiber elasticity index increased over 65% when Silube D 208-1 AGE was added to the guanidine relaxer.

Example 3

This example demonstrates compositions of the present invention and methods of using them for treating hair damage associated with a hair lightening process.

Table 3A below describes exemplary compositions of the invention in which compounds of formula (I) are formulated as micro-emulsions or nano-emulsions.

TABLE 3A

Exemplary emulsions containing compounds of formula (I)

| | | Wt % | |
|---|---|---|---|
| Ingredients | Intended Function | Formula 3A-1 | Formula 3A-2 |
| Deionized Water | Liquid Vehicle | 71.65 | 71.65 |
| Polysorbate 20 | Emulsifier | 1.00 | 1.00 |
| Crodafos CES | Emulsifier | 1.25 | 1.25 |
| Silmer ® 4EP J208 | Active (epoxysilicone) | 25.00 | — |
| Silmer ® EP J2 | Active (epoxysilicone) | — | 25.00 |
| Fragrance | Fragrance | 0.50 | 0.50 |
| Optiphen ® | Preservative | 0.50 | 0.50 |
| Sodium Benzoate | Preservative | 0.10 | 0.10 |
| pH | | 5.31 | 4.91 |

The emulsions in Table 3 may be prepared by microfluidization using a Microflidics Microfluidizer® processor Model 110 Y (High Pressure Pneumatic), with a collision/interaction chamber consisting of Z configuration at a pressure of 2500-23,000 psi (e.g., 14,000 psi), as described herein. By way of example, the emulsion process is carried out by adding deionized water to a S/S kettle, mixing with a sweep mixer at 15-20 Hz, and heating to 65-70° C. Next, an emulsifier (e.g., Liposorb O-20) is added, and mixing is continued with a sweep mixer at 15-20 Hz, and a Lightnin mixer at 15-20 Hz for 5-10 minutes or until homogenous, to produce a first phase. In a separate S/S kettle, an emulsifier (e.g., Crodafos CES), an epoxysilicone (e.g., Silmer® EP J2), a preservative (e.g., Optiphen®), and fragrance(s) are added, the mixture is heated to 65-70° C., and mixed until uniform, to produce a second phase. When the first and second phases are at 65-70° C., the second phase is added to the first phase (Main Kettle), and mixing is continued using a Homomixer or Lightnin mixer at 20-25 Hz for 25-30 minutes or until uniform. In a separate SS container, a preservative (e.g., sodium benzoate) is dissolved in an appropriate aqueous vehicle (e.g., deionized water), the resulting solution is added to the main batch, and the mixture is mixed for 10-15 minutes or until homogeneous. At 60-65° C., the mixture is passed through a Microflidics Microfluidizer® processor M-110Y (High Pressure Pneumatic), with a collision chamber consisting of Z configuration at a pressure of 2500-23,000 psi (preferably 14,000 psi), to produce an emulsion, which preferably has a particle size of from about 100 nm to about 250 nm.

Formula 3A-1 was tested as follows. 60 g of conventional 40 volume developer (Table 1B) and 30 g of conventional powder lightener (Table 1A) were placed in a bowl, and 7.5 g of an emulsion of Silmer® 4EP-J208 (Table 3A, Formula 3A-1) was added. This mixture was mixed well using an applicator brush until the mixture became smooth. The concentration of Silmer® 4 EP-J208 (active) in the emulsion was 1.92 wt %. The application procedure was as follows:

1. The untreated hair specimens were pre-tested on DMA using the intermittent stress relaxation test.
2. The pre-tested hair fibers (Caucasian, IMHAIR) were embedded on a 4 g of hair tress.
3. 32 g of a mixture prepared by combining 30 g (1 part) of control conventional bleaching powder (Table 1A), 60 g of the control developer 40 volume (Table 1B), and 7.5 g of bond multiplier (Table 3A, Formula 3A-1), was applied for 50 minutes. The hair tress was not wrapped in aluminum foil. The ratio of hair tress to bleaching mixture applied was 1:8.
4. The hair was rinsed with water for 3 minutes.
5. 5 g of non-conditioning shampoo (Table 1C) was applied for 3 minutes, the hair fibers were rinsed for 3 minutes and air-dried.
6. The stress for 0.50% strain as in step 1 and the ratio of the stress (force) were determined before and after treatment to determine the ISR.

The ingredients used in the lightening composition containing epoxysilicone are summarized below in Table 3B.

TABLE 3B

Depiction of ratios used in lightening composition containing epoxysilicone

| Ingredients | Ratio | Percentage |
| --- | --- | --- |
| Conventional Powder Lightener (Table 1A) | 30 | 30.77 |
| Conventional 40 Vol Developer (Table 1B) | 60 | 61.54 |
| Bond Multiplier (Table 3A, Formulation 3A-1) | 7.5 | 7.69 (1.92 wt % active) |

The test results demonstrating elasticity of the hair fibers treated with lightening composition containing epoxysilicone (Table 3B) are summarized below in Table 3C.

TABLE 3C

ISR data for fibers treated with lightening composition containing epoxysilicone emulsion (1.92 wt % active)

| Fiber | Un-Treated | Treated | ISR |
| --- | --- | --- | --- |
| 1 | 63.93 | 58.60 | 0.92 |
| 2 | 43.08 | 46.55 | 1.08 |
| 3 | 49.60 | 54.28 | 1.09 |
| 4 | 41.11 | 36.13 | 0.88 |
| 5 | 57.17 | 52.01 | 0.91 |
| 6 | 55.10 | 60.86 | 1.10 |
| 7 | 37.45 | 36.47 | 0.98 |
| 8 | 43.13 | 41.88 | 0.97 |
| 9 | 43.13 | 41.12 | 0.95 |
| 10 | 48.81 | 42.63 | 0.87 |
| 11 | 57.83 | 54.64 | 0.94 |
| 12 | 43.39 | 47.95 | 1.10 |
| Average | 48.64 | 47.76 | 0.98 |
| SD | 8.17 | 8.35 | 0.09 |
| CV | 16.80 | 17.47 | 9.00 |

Formula 3A-2 was tested as follows. 60 g of conventional 40 volume developer (Table 1B) and 30 g of conventional powder lightener (Table 1A) were placed in a bowl and 7.5 g of micro-emulsion of Silmer® EP-J2 (Table 3A, Formula 3A-2) were also added. This mixture was mixed well using a applicator brush until the mixture became smooth. The concentration of Silmer® EP-J2 (active) in the emulsion was 1.92 wt %. The application procedure was as follows:

The untreated hair specimens were pre-tested on DMA using the intermittent stress relaxation test.

1. The pre-tested hair fibers (Caucasian, IMHAIR) were embedded on a 4 g of hair tress.
2. 32 g of a mixture prepared by combining 30 g (1 part) of control conventional bleaching powder (Table 1A), 60 g (2 parts) of the control developer 40 volume (Table 1B), and 7.5 g of bond multiplier (Table 3A, Formula 3A-2), was applied for 50 minutes. The hair tress was not wrapped in aluminum foil. The ratio of hair tress to bleaching mixture applied was 1:8.
3. The hair was rinsed with water for 3 minutes.
4. 5 g of non-conditioning shampoo (Table 1C) was applied for 3 minutes, the hair fibers were rinsed for 3 minutes and air-dried.
5. The stress for 0.50% strain as in step 1 and the ratio of the stress (force) were determined before and after treatment to determine the ISR.

The ingredients used in the lightening composition containing epoxysilicone are summarized below in Table 3D.

TABLE 3D

Depiction of ratios used in lightening composition containing epoxysilicone

| Ingredients | Ratio | Percentage |
| --- | --- | --- |
| Conventional Powder Lightener (Table 1A) | 30 | 30.77 |
| Conventional 40 Vol Developer (Table 1B) | 60 | 61.54 |
| Bond Multiplier (Table 3A, Formulation 3A-2) | 7.5 | 7.69 (1.92 wt % active) |

The test results demonstrating elasticity of the hair fibers treated with lightening composition containing epoxysilicone (Table 3D) are summarized below in Table 3E.

TABLE 3E

ISR data for fibers treated with lightening composition containing epoxysilicone emulsion (1.92 wt % active)

| Fiber | Un-Treated | Treated | ISR |
| --- | --- | --- | --- |
| 1 | 41.62 | 38.24 | 0.92 |
| 2 | 51.03 | 57.92 | 1.14 |
| 3 | 39.31 | 42.20 | 1.07 |
| 4 | 52.19 | 54.01 | 1.04 |
| 5 | 40.53 | 46.79 | 1.15 |
| 6 | 56.57 | 60.60 | 1.07 |
| 7 | 43.50 | 42.82 | 0.98 |
| 8 | 62.07 | 65.50 | 1.06 |
| 9 | 40.94 | 41.85 | 1.02 |
| 10 | 44.59 | 51.92 | 1.16 |
| 11 | 42.11 | 42.65 | 1.01 |
| 12 | 42.38 | 34.66 | 0.82 |
| Average | 46.40 | 48.26 | 1.04 |
| SD | 7.31 | 9.61 | 0.10 |
| CV | 15.75 | 19.91 | 9.45 |

The test results for the epoxysilicone treated fibers relative to the control group (from Example 1) are shown below in Table 3F.

TABLE 3F

ISR of control fibers versus epoxysilicone treated fibers

| Fiber | Control Group (Ex. 1, Table 1D) | Epoxysilicone Treated (using Formula 3A-1) (Table 3C) | Epoxysilicone Treated (using Formula 3A-2) (Table 3E) |
|---|---|---|---|
| 1 | 0.87 | 0.92 | 0.92 |
| 2 | 0.85 | 1.08 | 1.14 |
| 3 | 0.88 | 1.09 | 1.07 |
| 4 | 0.91 | 0.88 | 1.04 |
| 5 | 0.83 | 0.91 | 1.15 |
| 6 | 0.82 | 1.10 | 1.07 |
| 7 | 0.86 | 0.98 | 0.98 |
| 8 | 0.83 | 0.97 | 1.06 |
| 9 | 0.90 | 0.95 | 1.02 |
| 10 | 0.94 | 0.87 | 1.16 |
| 11 | 0.81 | 0.94 | 1.01 |
| 12 | 0.98 | 1.10 | 0.82 |
| Ave | 0.87 | 0.98 | 1.04 |

The epoxysilicone treated hair fibers exhibited significantly greater strength relative to control, demonstrating a significant reduction in damage associated with a conventional hair lightening process.

Example 4

This example demonstrates compositions of the present invention and methods of using them for treating hair damage associated with two consecutive lightening procedures.

A group of control hair fibers was treated with conventional powder lightener (Table 1A) and a conventional 40 volume developer (Table 1B). The mixing ratio of the hydrogen peroxide developer and the powder lightener was 2:1. The application procedure was as follows:

1. The untreated hair specimens were pre-tested on DMA using the intermittent stress relaxation test.
2. The pre-tested hair fibers (Caucasian, IMHAIR) were embedded on a 4 g of hair tress.
3. 32 g of a mixture prepared by combining 30 g (1 part) of control conventional bleaching powder (Table 1A) and 2 parts (60.0 g) of the control 40 volume developer (Table 1B) was applied for 50 minutes. The hair tress was not wrapped in aluminum foil. The ratio of hair tress to bleaching mixture applied was 1:8.
4. The hair was rinsed with water for 3 minutes.
5. 5 g of non-conditioning shampoo (Table 1C) was applied for 3 minutes, the hair fibers were rinsed for 3 minutes and air-dried.
6. The fibers were again treated with steps 3 to 5 for double treatment.
7. The dried fibers were kept at room temperature overnight and stress for 0.50% strain of wet fibers was determined again, as in step 1. The ratio of the stress (force) before and after two treatments was determined as the ISR for double treated hair.

The ISR test results for the control fibers are summarized below in Table 4A.

TABLE 4A

ISR data for hair fibers subjected to two conventional lightening procedures

| Fiber | Strength Before Treatment | Strength After Two Treatments | ISR |
|---|---|---|---|
| 1 | 45.70 | 34.72 | 0.76 |
| 2 | 39.83 | 25.62 | 0.64 |
| 3 | 26.54 | 12.77 | 0.48 |
| 4 | 47.36 | 31.86 | 0.67 |
| 5 | 68.02 | 34.90 | 0.51 |
| 6 | 57.36 | 31.76 | 0.55 |
| 7 | 50.45 | 41.40 | 0.82 |
| 8 | 48.17 | 26.62 | 0.55 |
| 9 | 66.98 | 38.69 | 0.58 |
| 10 | 59.89 | 42.08 | 0.70 |
| 11 | 68.49 | 47.11 | 0.69 |
| 12 | 47.21 | 27.48 | 0.58 |
| 13 | 51.71 | 34.38 | 0.66 |
| Average | 51.24 | 32.29 | 0.63 |
| SD | 11.40 | 9.61 | 0.10 |
| Coefficient of Variance | 22.26 | 29.76 | 15.73 |

For the epoxysilicone treated hair fibers, the same general procedure was used, except that an epoxysilicone emulsion (Table 3A, Formula 3A-2) was added to the lightening composition before application, as follows.

1. The untreated hair specimens were pre-tested on DMA using the intermittent stress relaxation test.
2. The pre-tested hair fibers (Caucasian, IMHAIR) were embedded on a 4 g of hair tress.
3. 32 g of a mixture prepared by combining 30 g (1 part) of control conventional bleaching powder (Table 1A), 2 parts (60.0 g) of the control 40 volume developer (Table 1B), and 7.5 g of bond multiplier (Table 3A, Formula 3A-2) (1.92 wt % active, see Table 3D), was applied for 50 minutes. The hair tress was not wrapped in aluminum foil. The ratio of hair tress to bleaching mixture applied was 1:8.
4. The hair was rinsed with water for 3 minutes.
5. 5 g of non-conditioning shampoo (Table 1C) was applied for 3 minutes, the hair fibers were rinsed for 3 minutes and air-dried.
6. The fibers were again treated with steps 3 to 5 for double treatment.
7. The dried fibers were kept at room temperature overnight and stress for 0.50% strain of wet fibers was determined again, as in step 1. The ratio of the stress (force) before and after two treatments was determined as the ISR for double treated hair.

The ISR test results for the epoxysilicone treated hair fibers subjected to consecutive lightening procedures are summarized below in Table 4B.

TABLE 4B

ISR data for epoxysilicone treated hair fibers subjected to two conventional lightening procedures

| Fiber | Strength Before Treatment | Strength After Two Treatments | ISR |
|---|---|---|---|
| 1 | 44.10 | 36.81 | 0.84 |
| 2 | 55.50 | 48.28 | 0.87 |
| 3 | 50.43 | 43.85 | 0.87 |
| 4 | 74.88 | 56.73 | 0.76 |
| 5 | 31.25 | 32.39 | 1.04 |
| 6 | 50.81 | 35.59 | 0.70 |
| 7 | 63.15 | 49.33 | 0.78 |

TABLE 4B-continued

ISR data for epoxysilicone treated hair fibers subjected to two conventional lightening procedures

| Fiber | Strength Before Treatment | Strength After Two Treatments | ISR |
|---|---|---|---|
| 8 | 55.66 | 58.95 | 1.06 |
| 9 | 64.37 | 50.66 | 0.79 |
| 10 | 47.17 | 47.78 | 1.01 |
| 11 | 54.18 | 44.78 | 0.83 |
| 12 | 55.21 | 41.62 | 0.75 |
| Ave | 53.98 | 44.36 | 0.86 |
| SD | 10.11 | 8.58 | 0.12 |
| CC | 18.73 | 19.34 | 13.85 |

The epoxysilicone treated hair fibers exhibited significantly greater strength relative to control, demonstrating a significant reduction in damage associated with two consecutive applications of a conventional hair lightening process.

Example 5

This example demonstrates compositions of the present invention containing various concentrations of epoxysilicone, and methods of using them for treating hair damage associated with a lightening process.

Table 5A below describes exemplary compositions of the invention in the form of micro-emulsions or nano-emulsions.

TABLE 5A

Exemplary emulsions containing a compound of formula (I)

| | Wt % | | |
|---|---|---|---|
| Ingredients | Formula 5A-1 | Formula 5A-2 | Formula 5A-3 |
| Deionized Water | 86.15 | 76.15 | 73.65 |
| Tween 80 | 1.00 | 1.00 | 1.00 |
| Crodofos CES | 1.25 | 1.25 | 1.25 |
| Silmer ® EP J2 (epoxysilicone, active) | 10.00 | 20.00 | 22.50 |
| Ruby Guava Fragrance | 0.50 | 0.50 | 0.50 |
| N16279 Carruba | | | |
| Optiphen ® | 0.50 | 0.50 | 0.50 |
| Sodium Benzoate | 0.10 | 0.10 | 0.10 |
| Deionized Water | 0.50 | 0.50 | 0.50 |
| Appearance | milky | milky | milky |
| PH | 4.20 | 3.54 | 4.22 |

Formula 5A-1 was tested as follows. 60 g of conventional 40 volume developer (Table 1B) and 30 g of conventional powder lightener (Table 1A) were placed in a bowl, and 7.5 g of an emulsion of Silmer® EP-J2 (Table 5A, Formula 5A-1) was added. This mixture was mixed well using an applicator brush until the mixture became smooth. The mixture had an active Silmer® EP-J2 concentration of 0.77 wt %. The application procedure was as follows:

1. The untreated hair specimens were pre-tested on DMA using the intermittent stress relaxation test.
2. The pre-tested hair fibers (Caucasian, IMHAIR) were embedded on a 4 g of hair tress.
3. 32 g of a mixture prepared by combining 30 g (1 part) of control conventional bleaching powder (Table 1A), 60 g (2 parts) of the control developer 40 volume (Table 1B), and 7.5 g of bond multiplier (Table 5A, Formula 5A-1), was applied for 50 minutes. The hair tress was not wrapped in aluminum foil. The ratio of hair tress to bleaching mixture applied was 1:8.
4. The hair was rinsed with water for 3 minutes.
5. 5 g of non-conditioning shampoo (Table 1C) was applied for 3 minutes, the hair fibers were rinsed for 3 minutes and air-dried.
6. The stress for 0.50% strain as in step 1 and the ratio of the stress (force) were determined before and after treatment to determine the ISR.

The ingredients used in the lightening composition containing epoxysilicone are summarized below in Table 5B.

TABLE 5B

Depiction of ratios used in lightening composition containing expoxysilicone

| Ingredients | Ratio | Percentage |
|---|---|---|
| Conventional Powder Lightener (Table 1A) | 30 | 30.77 |
| Conventional 40 Vol Developer (Table 1B) | 60 | 61.54 |
| Bond Multiplier (Table 5A, Formula 5A-1) | 7.5 | 7.69 (0.77 wt % active) |

The test results for the hair fibers treated with lightening composition containing epoxysilicone (Table 5B) are summarized below in Table 5C.

TABLE 5C

ISR data for fibers treated with conventional lightening composition containing Silmer ® EP J2 (Table 5B, 0.77 wt % active)

| Fiber | Un-Treated | Treated | ISR |
|---|---|---|---|
| 1 | 56.82 | 40.29 | 0.71 |
| 2 | 59.21 | 52.74 | 0.89 |
| 3 | 58.32 | 58.67 | 1.01 |
| 4 | 49.26 | 46.79 | 0.95 |
| 5 | 43.18 | 40.86 | 0.95 |
| 6 | 59.01 | 50.43 | 0.85 |
| 7 | 44.81 | 41.98 | 0.94 |
| 8 | 61.16 | 54.17 | 0.89 |
| 9 | 52.26 | 43.61 | 0.83 |
| 10 | 51.77 | 38.82 | 0.75 |
| 11 | 46.70 | 49.07 | 1.05 |
| 12 | 41.33 | 41.26 | 1.00 |
| 13 | 60.98 | 51.69 | 0.85 |
| Average | 52.68 | 46.95 | 0.90 |
| SD | 7.08 | 6.31 | 0.10 |
| CV | 13.45 | 13.44 | 11.07 |

Formula 5A-2 was tested as follows. 60 g of conventional 40 volume developer (Table 1B) and 30 g of conventional powder lightener (Table 1A) were placed in a bowl, and 7.5 g of an emulsion of Silmer® EP-J2 (Table 5A, Formula 5A-2) was added. This mixture was mixed well using a applicator brush until the mixture became smooth. The mixture had an active Silmer® EP-J2 concentration of 1.54 wt %. The application procedure was as follows:

1. The untreated hair specimens were pre-tested on DMA using the intermittent stress relaxation test.
2. The pre-tested hair fibers (Caucasian, IMHAIR) were embedded on a 4 g of hair tress.
3. 32 g of a mixture prepared by combining 30 g (1 part) of control conventional bleaching powder (Table 1A), 60 g (2 parts) of the control developer 40 Volume (Table 1B), and 7.5 g of bond multiplier (Table 5A, Formula 5A-2), was applied for 50 minutes. The hair tress was not wrapped in aluminum foil. The ratio of hair tress to bleaching mixture applied was 1:8.
4. The hair was rinsed with water for 3 minutes.

5. 5 g of non-conditioning shampoo (Table 1C) was applied for 3 minutes, the hair fibers were rinsed for 3 minutes and air-dried.
6. The stress for 0.50% strain as in step 1 and the ratio of the stress (force) were determined before and after treatment to determine the ISR.

The ingredients used in the lightening composition containing epoxysilicone are summarized below in Table 5D.

TABLE 5D

Depiction of ratios used in lightening composition containing expoxysilicone

| Ingredients | Ratio | Percentage |
|---|---|---|
| Conventional Powder Lightener (Table 1A) | 30 | 30.77 |
| Conventional 40 Vol Developer (Table 1B) | 60 | 61.54 |
| Bond Multiplier (Table 5A, Formula 5A-2) | 7.5 | 7.69 (1.54 wt % active) |

The test results for the hair fibers treated with lightening composition containing epoxysilicone (Table 5D) are summarized below in Table 5E.

TABLE 5E

ISR data for fibers treated with conventional lightening composition containing Silmer ® EP J2 (Table 5D, 1.54 wt % active)

| Fiber | Un-Treated | Treated | ISR |
|---|---|---|---|
| 1 | 63.41 | 64.09 | 1.01 |
| 2 | 71.78 | 59.42 | 0.83 |
| 3 | 57.19 | 45.29 | 0.79 |
| 4 | 55.93 | 49.27 | 0.88 |
| 5 | 62.49 | 47.98 | 0.77 |
| 6 | 44.87 | 46.97 | 1.05 |
| 7 | 59.30 | 56.41 | 0.95 |
| 8 | 40.52 | 39.84 | 0.98 |
| 9 | 50.89 | 57.12 | 1.12 |
| 10 | 50.20 | 44.05 | 0.88 |
| 11 | 47.04 | 45.35 | 0.96 |
| 12 | 31.16 | 35.46 | 1.14 |
| Average | 52.90 | 49.27 | 0.95 |
| SD | 11.13 | 8.42 | 0.12 |
| CV | 21.05 | 17.09 | 12.80 |

Formula 5A-3 was tested as follows: 60 g of conventional 40 volume developer formula (Table 1B) and 30 g of conventional powder lightener (Table 1A) were placed in a bowl, and 7.5 g of an emulsion of Silmer® EP-J2 (Table 5A, Formula 5A-3) was added. This mixture was mixed well using a applicator brush until the mixture became smooth. The mixture has an active Silmer® EP-J2 concentration of 1.73 wt %. The application procedure was as follows:
1. The untreated hair specimens were pre-tested on DMA using the intermittent stress relaxation test.
2. The pre-tested hair fibers (Caucasian, IMHAIR) were embedded on a 4 g of hair tress.
3. 32 g of a mixture prepared by combining 30 g (1 part) of control conventional bleaching powder (Table 1A), 60 g (2 parts) of the control developer 40 volume (Table 1B), and 7.5 g of bond multiplier (Table 5A, Formula 5A-3), was applied for 50 minutes. The hair tress was not wrapped in aluminum foil. The ratio of hair tress to bleaching mixture applied was 1:8.
4. The hair was rinsed with water for 3 minutes.
5. 5 g of non-conditioning shampoo (Table 1C) was applied for 3 minutes, the hair fibers were rinsed for 3 minutes and air-dried.
6. The stress for 0.50% strain as in step 1 and the ratio of the stress (force) were determined before and after treatment to determine the ISR.

The ingredients used in the lightening composition containing epoxysilicone are summarized below in Table 5F.

TABLE 5F

Depiction of ratios used in lightening composition containing expoxysilicone

| Ingredients | Ratio | Percentage |
|---|---|---|
| Conventional Powder Lightener (Table 1A) | 30 | 30.77 |
| Conventional 40 Vol Developer (Table 1B) | 60 | 61.54 |
| Bond Multiplier (Table 5A, Formula 5A-3) | 7.5 | 7.69 (1.73 wt % active) |

The test results for the hair fibers treated with lightening composition containing epoxysilicone (Table 5F) are summarized below in Table 5G.

TABLE 5G

ISR data for fibers treated with conventional lightening composition containing Silmer ® EP J2 (Table 5F, 1.73 wt % active)

| Fiber | Un-Treated | Treated | ISR |
|---|---|---|---|
| 1 | 63.12 | 55.88 | 0.89 |
| 2 | 49.14 | 43.53 | 0.89 |
| 3 | 46.11 | 39.66 | 0.86 |
| 4 | 62.94 | 59.58 | 0.95 |
| 5 | 62.03 | 66.72 | 1.08 |
| 6 | 56.56 | 55.03 | 0.97 |
| 7 | 59.60 | 58.00 | 0.97 |
| 8 | 33.61 | 25.39 | 0.76 |
| 9 | 50.86 | 49.49 | 0.97 |
| 10 | 53.87 | 46.15 | 0.86 |
| 11 | 70.83 | 56.64 | 0.80 |
| 12 | 59.41 | 48.99 | 0.82 |
| Average | 55.67 | 50.42 | 0.90 |
| SD | 9.80 | 10.90 | 0.09 |
| CV | 17.60 | 21.62 | 10.07 |

The test results for the epoxysilicone treated fibers relative to control group (from Example 1) are summarized below in Table 5H.

TABLE 5H

ISR of control fibers versus epoxysilicone treated fibers

| Emulsion Used | No. of Fibers | Epoxysilicone Concentration for Emulsion | Epoxysilicone Concentration in Lightening Composition | Average ISR |
|---|---|---|---|---|
| Control (Ex. 1, Table 1D) | 12 | 0.00 wt % | 0.00 wt % | 0.87 |
| Table 5A, Formula 5A-1 | 13 | 10.00 wt % | 0.77 wt % | 0.90 |
| Table 5A, Formula 5A-2 | 12 | 20.00 wt % | 1.54 wt % | 0.95 |
| Table 5A, Formula 5A-3 | 12 | 22.50 wt % | 1.73 wt % | 0.90 |

The epoxysilicone treated hair fibers exhibited significantly greater strength relative to control, demonstrating a significant reduction in damage associated with a conventional hair lightening process.

Example 6

This example demonstrates compositions of the present invention and methods of using them for treating hair damage associated with a hair relaxing process.

The control group of hair fibers prepared in Example 2 was used as the control for this study. The epoxysilicone treated hair fibers were subjected to the same relaxing process that was used for the control fibers, except that emulsion Formula 3A-2 (Example 3, Table 3A) was added to the relaxer system as shown below in Table 6A.

TABLE 6A

Guanidine hydroxide relaxer containing epoxysilicone

| Components | Wt % |
|---|---|
| Non-conditioning Calcium Hydroxide Cream (Table 2A) | 75.35 |
| Non-Conditioning Liquid Activator (Table 2B) | 20.65 |
| Emulsion of Silmer® EP J2 (Formula 3A-2, Ex. 3, Table 3A) | 4.00 (1.00 wt % active) |

The ISR data at 100% RH for the hair fibers treated with the relaxer system containing epoxysilicone (Table 6A) is summarized below in Table 6B.

TABLE 6B

ISR data at 100% RH for fibers treated with guanidine hydroxide relaxer containing 4.0 wt % of Silmer® EP J2 emulsion (wet fibers)

| Fiber | Strength Before Treatment | Strength After Treatment | Intermittent Stress Relaxation |
|---|---|---|---|
| 1 | 50.37 | 29.93 | 0.59 |
| 2 | 55.04 | 37.96 | 0.69 |
| 3 | 55.04 | 34.68 | 0.63 |
| 4 | 64.21 | 41.66 | 0.65 |
| 5 | 26.71 | 18.70 | 0.70 |
| 6 | 64.99 | 39.57 | 0.61 |
| 7 | 56.99 | 20.23 | 0.66 |
| 8 | 60.35 | 37.35 | 0.62 |
| 9 | 73.24 | 43.27 | 0.59 |
| 10 | 70.54 | 43.27 | 0.61 |
| 11 | 30.43 | 22.05 | 0.72 |
| 12 | 69.73 | 56.40 | 0.81 |
| 13 | 62.78 | 39.97 | 0.64 |
| Average | 56.95 | 35.77 | 0.66 |
| SD | 14.27 | 10.68 | 0.06 |
| CV | 25.06 | 29.85 | 9.41 |

The epoxysilicone treated hair fibers exhibited significantly greater strength relative to control, demonstrating a significant reduction in damage associated with a conventional hair relaxing process. The fiber elasticity index increased by over 60% when 1.0 wt % of Silmer® EP J2 was added as an emulsion to the guanidine relaxer.

Example 7

This example demonstrates compositions of the present invention and methods of using them for treating hair damage associated with a permanent hair coloring process.

Tables 7A and 7B below describe a conventional permanent coloring composition and a conventional hydrogen peroxide developer, respectively.

TABLE 7A

Conventional permanent color 6 RR

| Ingredient | Wt % |
|---|---|
| Water | 41.7050 |
| Rapithix A-60 | 1.0000 |
| Veersene 220 (Tetrasodium EDTA) | 0.9600 |
| Sodium Metabisulfite | 0.3000 |
| Erythorbic Acid | 0.2000 |
| Cocamide DIPA | 0.5000 |
| Ethoxydiglycol | 5.0000 |
| Rodol Red # 9 | 3.000 |
| Rodol 2A3PYR | 0.200 |
| HC Yellow # 2 | 1.000 |
| Rodol D | 0.080 |
| Fatty Alcohol | 13.3000 |
| Liposorb S-20 | 0.3940 |
| Lipocol SC-20 | 0.2660 |
| Lipocol O-10 | 0.04 |
| Oleic Acid | 2.0000 |
| Lipocol SC-20 | 2.4000 |
| Carsoquat CT-429 | 2.1550 |
| Lauryl Pyrrolidone | 0.5000 |
| Empicol AL30/AF3 | 12.0000 |
| Crodafos HCE (Oleth-5 Phosphate and Dioleyl Phosphate) | 2.0000 |
| Perfume 57779M | 1.5000 |
| Monoethanolamine | 4.0000 |
| Ammonium Acetate | 0.5000 |
| Ammonium Hydroxide 26 Be | 5.0000 |

TABLE 7B

Conventional Hydrogen Peroxide Developer 20 Volume

| Ingredient | Wt % |
|---|---|
| Water | 67.6400 |
| Etidronic Acid (60%) | 0.1000 |
| Sodium Stannate | 0.1000 |
| Lipocol-C (Cetyl Alcohol) | 3.5000 |
| Procol CA - 10 | 1.5000 |
| Anti Foam A Compound | 0.0500 |
| Carsoquat CT-429 | 2.5000 |
| Aculyn 46 Polymer | 0.2100 |
| Hydrogen Peroxide 50% (FMC) | 12.0000 |
| Phosphoric Acid (85%) | 0.2000 |
| Sodium Dihydrogen Phosphate | 0.2000 | pH = 3.51,
Viscosity = 3,000 cps

A group of control hair fibers was treated with conventional permanent hair color 6RR (Table 7A) and a conventional 20 volume developer (Table 7B). The mixing ratio of the hydrogen peroxide developer and the permanent color was 1:1. The application procedure was as follows:
1. The untreated hair specimens were pre-tested on DMA using the intermittent stress relaxation test.
2. The pre-tested hair fibers (Caucasian, IMHAIR) were embedded on a 2 g of hair tress.
3. 6.0 g of the mixture of 1 part of control conventional permanent color (Table 7A) and 1 part of the control 20 volume developer (Table 7B) was applied for 45 minutes.
4. The hair was rinsed with water for 3 minutes.
5. 5 g of non-conditioning shampoo (Ex. 1, Table 1C) was applied for 3 minutes, the hair fibers were rinsed for 3 minutes and air-dried.
6. The stress for 0.50% strain as in step 1 and the ratio of the stress (force) were determined before and after treatment to determine the ISR.

The ISR test results for the control fibers are summarized below in Table 7C.

TABLE 7C

ISR data for hair fibers treated with conventional permanent color 6RR

| Fiber | Strength Before Treatment | Strength After Treatment | ISR |
|---|---|---|---|
| 1 | 67.98 | 62.91 | 0.93 |
| 2 | 57.56 | 53.52 | 0.93 |
| 3 | 49.41 | 46.58 | 0.94 |
| 4 | 69.30 | 50.98 | 0.74 |
| 5 | 68.96 | 52.47 | 0.76 |
| 6 | 56.43 | 46.67 | 0.83 |
| 7 | 65.90 | 50.74 | 0.77 |
| 8 | 57.81 | 53.66 | 0.93 |
| 9 | 69.96 | 68.08 | 0.97 |
| 10 | 47.21 | 45.21 | 0.96 |
| 11 | 57.59 | 42.61 | 0.74 |
| 12 | 69.68 | 70.10 | 1.01 |
| Average | 61.48 | 53.63 | 0.88 |
| Standard Deviation | 8.19 | 8.91 | 0.10 |
| Coefficient of Variation | 13.32 | 16.61 | 11.44 |

For the epoxysilicone treated hair fibers, two different epoxysilicone concentrations were tested. In one experiment, 10 g of conventional 20 volume developer (Table 7B) and 10 g of conventional permanent hair color 6RR (Table 7A) were placed in a bowl, and 2.5 g of bond multiplier Formula 1E-1 (Ex. 1, Table 1E) was added. This mixture was mixed well using a applicator brush until the mixture became smooth. The mixture had an active Silube D 208-1AGE concentration of 8.33 wt %. The application procedure was as follow:

1. The untreated hair specimens were pre-tested on DMA using the intermittent stress relaxation test.
2. The pre-tested hair fibers (Caucasian, IMHAIR) were embedded on a 2 g of hair tress.
3. 6.0 g of the mixture of 1 part of control conventional 20 volume developer (Table 7B), 10 g of the control permanent color 6RR (Table 7A), and 2.5 g of bond multiplier (Formula 1E-1, Ex. 1, Table 1E) was applied for 45 minutes.
4. The hair was rinsed with water for 3 minutes.
5. 5 g of non-conditioning shampoo (Table 1C) was applied for 3 minutes, the hair fibers were rinsed for 3 minutes and air-dried.
6. The stress for 0.50% strain as in step 1 and the ratio of the stress (force) were determined before and after treatment to determine the ISR.

The ingredients used in the permanent coloring composition containing epoxysilicone according to the above procedure are summarized below in Table 7D.

TABLE 7D

Depiction of ratios used in permanent coloring composition containing expoxysilicone

| Ingredients | Ratio | Wt % |
|---|---|---|
| Conventional Permanent Hair Color 6 RR (Table 7A) | 10 | 44.44 |
| Conventional 20 Vol Developer (Table 7B) | 10 | 44.44 |
| Bond Regenerator (Formula 1E-1, Ex. 1, Table 1E) | 2.5 | 11.12 (8.33 wt % active) |

The test results for the hair fibers treated with permanent coloring composition containing epoxysilicone (Table 7D) are summarized below in Table 7E.

TABLE 7E

ISR data for fibers treated with permanent hair coloring composition containing Silube D 208-1AGE (8.33 wt % active)

| Fiber | Un-Treated | Treated | ISR |
|---|---|---|---|
| 1 | 39.74 | 42.74 | 1.08 |
| 2 | 43.61 | 52.06 | 1.19 |
| 3 | 63.03 | 60.45 | 0.96 |
| 4 | 53.12 | 49.87 | 0.94 |
| 5 | 57.52 | 54.66 | 0.95 |
| 6 | 61.65 | 61.95 | 1.01 |
| 7 | 63.42 | 57.13 | 0.90 |
| 8 | 58.61 | 53.89 | 0.92 |
| 9 | 58.85 | 53.14 | 0.90 |
| 10 | 57.84 | 57.82 | 1.00 |
| 11 | 48.84 | 59.70 | 1.21 |
| 12 | 51.94 | 49.52 | 0.95 |
| 13 | 66.48 | 63.53 | 0.96 |
| 14 | 48.78 | 43.76 | 0.90 |
| 15 | 49.15 | 44.85 | 0.91 |
| Average | 54.84 | 53.67 | 0.99 |
| SD | 7.74 | 6.59 | 0.10 |
| CV | 14.12 | 12.28 | 10.18 |

In another experiment, the procedure described immediately above was performed, except that Formula 1E-2 (Ex. 1, Table 1E) was used as the bond multiplier. The ingredients used in the permanent coloring composition containing epoxysilicone used in this procedure are summarized below in Table 7F.

TABLE 7F

Depiction of ratios used in permanent coloring composition containing expoxysilicone

| Ingredients | Ratio | Wt % |
|---|---|---|
| Conventional Permanent Hair Color 6 RR (Table 7A) | 10 | 44.44 |
| Conventional 20 Vol Developer (Table 7B) | 10 | 44.44 |
| Bond Multiplier (Formula 1E-2, Ex. 1, Table 1E) | 2.5 | 11.12 (2.78 wt % active) |

The test results for the hair fibers treated with permanent coloring composition containing epoxysilicone (Table 7F) are summarized below in Table 7G.

TABLE 7G

ISR data for fibers treated with permanent hair coloring composition containing Silube D 208-1AGE (2.78 wt % active)

| Fiber | Un-Treated | Treated | ISR |
|---|---|---|---|
| 1 | 69.30 | 61.77 | 0.89 |
| 2 | 63.98 | 69.14 | 1.08 |
| 3 | 63.16 | 67.03 | 1.06 |
| 4 | 72.05 | 69.80 | 0.97 |
| 5 | 66.83 | 59.61 | 0.89 |
| 6 | 54.53 | 55.78 | 1.02 |
| 7 | 58.72 | 58.75 | 1.00 |
| 8 | 63.34 | 63.28 | 1.00 |
| 9 | 63.54 | 55.39 | 0.87 |
| 10 | 40.39 | 44.99 | 1.11 |
| 11 | 49.73 | 46.23 | 0.93 |
| 12 | 65.88 | 65.74 | 1.00 |
| Average | 60.95 | 59.79 | 0.99 |
| SD | 8.91 | 8.15 | 0.08 |
| CV | 14.62 | 13.63 | 7.91 |

The epoxysilicone treated hair fibers exhibited significantly greater strength relative to control, demonstrating a significant reduction in damage associated with a conventional permanent coloring process.

Example 8

This example demonstrates compositions of the present invention and methods of using them for treating hair damage associated with a permanent hair coloring process.

The control group of hair fibers prepared in Example 7 was used as the control for this study. For the epoxysilicone treated hair fibers, 10 g of conventional 20 volume developer formula (Table 7B) and 10 g of conventional permanent hair color 6RR (Table 7A) were placed in a bowl and 2.5 g of bond multiplier Formula 3A-2 (Example 3, Table 3A) was added. This mixture was mixed well using an applicator brush until the mixture became smooth. The mixture had an active Silmer® EP J2 concentration of 2.78 wt %. The application procedure was as follows:
1. The untreated hair specimens were pre-tested on DMA using the intermittent stress relaxation test.
2. The pre-tested hair fibers (Caucasian, IMHAIR) were embedded on a 2 g of hair tress.
3. 6.0 g of the mixture of 1 part of control conventional 20 volume developer (Table 7B), 10 g of the control permanent color 6RR (Table 7A), and 2.5 g of bond multiplier (Formula 3A-2, Ex. 3, Table 3A), was applied for 45 minutes.
4. The hair was rinsed with water for 3 minutes.
5. 5 g of non-conditioning shampoo (Ex. 1, Table 1C) was applied for 3 minutes, the hair fibers were rinsed for 3 minutes, and air-dried.
6. The stress for 0.50% strain as in step 1 and the ratio of the stress (force) were determined before and after treatment to determine the ISR.

The ingredients used in the permanent coloring composition containing epoxysilicone according to the above procedure are summarized below in Table 8A.

TABLE 8A

Permanent coloring composition containing expoxysilicone

| Ingredients | Ratio | Wt % |
|---|---|---|
| Conventional Permanent Hair Color 6 RR (Table 7A) | 10 | 44.44 |
| Conventional 20 Vol Developer (Table 7B) | 10 | 44.44 |
| Bond Multiplier (Formula 3A-2, Ex. 3, Table 3A) | 2.5 | 11.12 (2.78 wt % active) |

The test results for the hair fibers treated with permanent coloring composition containing epoxysilicone (Table 8A) are summarized below in Table 8B.

TABLE 8B

ISR data for fibers treated with permanent hair coloring composition containing epoxysilicone (2.78 wt % active)

| Fiber | Strength Before Treatment | Strength After Treatment | Intermittent Stress Relaxation |
|---|---|---|---|
| 1 | 65.08 | 61.19 | 0.94 |
| 2 | 61.17 | 60.28 | 0.99 |
| 3 | 73.48 | 61.25 | 0.83 |
| 4 | 53.19 | 52.94 | 1.00 |
| 5 | 54.94 | 59.09 | 1.08 |
| 6 | 60.34 | 60.25 | 1.00 |
| 7 | 68.59 | 66.92 | 0.98 |
| 8 | 55.38 | 50.85 | 0.92 |

TABLE 8B-continued

ISR data for fibers treated with permanent hair coloring composition containing epoxysilicone (2.78 wt % active)

| Fiber | Strength Before Treatment | Strength After Treatment | Intermittent Stress Relaxation |
|---|---|---|---|
| 9 | 68.25 | 68.58 | 1.01 |
| 10 | 39.66 | 42.45 | 1.07 |
| 11 | 59.79 | 62.13 | 1.04 |
| 12 | 52.00 | 49.40 | 0.95 |
| 13 | 60.92 | 63.12 | 1.04 |
| Average | 59.44 | 58.34 | 0.99 |
| SD | 8.75 | 7.40 | 0.07 |
| CV | 14.72 | 12.69 | 6.83 |

The epoxysilicone treated hair fibers exhibited significantly greater strength relative to control, demonstrating a significant reduction in damage associated with a conventional hair lightening process.

Example 9

This example demonstrates compositions of the present invention and methods of using them for treating hair damage associated with a hair lightening process.

Table 9A describes an emulsion containing Silmer® EP Di-10 (Siltech LLC).

TABLE 9A

Emulsion containing Silmer EP Di-10

| Ingredients | Wt % |
|---|---|
| Deionized Water | 81.65 |
| Polysorbate 20 | 1.00 |
| Crodafos CES | 1.25 |
| Silmer ® EP Di-10 | 15.00 |
| Fragrance | 0.50 |
| Optiphen | 0.50 |
| Sodium Benzoate | 0.10 |
| pH | 4.56 |

60 g of conventional 40 volume developer (Table 1B) and 30 g of conventional powder lightener (Table 1A) were placed in a bowl, and 7.5 g of a micro-emulsion of Silmer® EP Di-10 (Table 9A) were also added. This mixture was mixed well using an applicator brush until the mixture became smooth. The resulting bleaching composition had an active Silmer® EP Di-10 concentration of 1.15%. The components and ratios used in the bleaching composition are summarized below in Table 9B.

TABLE 9B

Bleaching composition containing epoxysilicone

| Ingredients | Ratio | Percentage |
|---|---|---|
| Conventional Powder Lightener (Table 1A) | 30 | 30.77 |
| Conventional 40 Vol Developer (Table 1B) | 60 | 61.54 |
| Micro-emulsion containing 15.0% Silmer EP Di-10 (Table 9A) | 7.5 | 7.69 (1.15 wt % active) |

The application procedure was as follows:
1. The untreated hair specimens were pre-tested on DMA using the ISR test.
2. The pre-tested hair fibers (Caucasian, IMHAIR) were embedded on a 4 g hair tress.
3. 32 g of the bleaching mixture was applied to hair embedded in the 4 g tress for 50 minutes. The hair tress was not wrapped in an aluminum foil. The ratio of hair tress to bleaching mixture applied was 1:8.

4. After 50 minutes of processing, the hair was rinsed with lukewarm water for 3 minutes.
5. A 5 g of non-conditioning shampoo (Table 1C) was applied to the tress for 3 minutes and rinsed for 3 minutes and air-dried.
6. The stress at 0.50% strain was determined and the ratio of the stress (force) before and after treatment was determined by ISR.

The elasticity of fibers after treatment with this mixture (Table 9B) is shown in Table 9C.

TABLE 9C

ISR data for fibers treated with hair lightening mixture containing epoxysilicone (Table 9B)

| Fiber | Un-Treated | Treated | ISR |
|---|---|---|---|
| 1 | 48.20 | 54.69 | 1.13 |
| 2 | 75.98 | 72.80 | 0.96 |
| 3 | 50.19 | 46.05 | 0.92 |
| 4 | 59.48 | 58.40 | 0.98 |
| 5 | 51.88 | 60.00 | 1.16 |
| 6 | 59.67 | 59.83 | 1.00 |
| 7 | 67.38 | 62.22 | 0.92 |
| 8 | 49.58 | 47.64 | 0.96 |
| 9 | 55.52 | 49.71 | 0.90 |
| 10 | 51.86 | 44.93 | 0.87 |
| 11 | 64.09 | 59.54 | 0.93 |
| 12 | 71.42 | 66.14 | 0.93 |
| 13 | 60.45 | 55.01 | 0.91 |
| Ave | 58.90 | 56.69 | 0.97 |
| SD | 8.84 | 8.16 | 0.09 |
| CV | 15.01 | 14.40 | 8.93 |

The ISR data for two groups of hair fibers, one treated with a conventional bleaching composition without epoxysilicone (control), and one treated with the bleaching composition of Table 9B, are shown in Table 9D.

TABLE 9D

ISR data for two fiber groups, one treated with a conventional bleaching mixture (control), and one treated with a bleaching mixture containing Silmer EP Di-10.

| Fiber | Bleaching Mixture Containing Conventional Powder Lightener (Table 1A) and 40 Volume Developer (Table 1B) (Control) | Bleaching Mixture Containing Powder Lightener. 40 Volume Developer, and Silmer ® EP Di-10 (Table 9B) |
|---|---|---|
| 1 | 0.87 | 1.13 |
| 2 | 0.85 | 0.96 |
| 3 | 0.88 | 0.92 |
| 4 | 0.91 | 0.98 |
| 5 | 0.83 | 1.16 |
| 6 | 0.82 | 1.00 |
| 7 | 0.86 | 0.92 |
| 8 | 0.83 | 0.96 |
| 9 | 0.90 | 0.90 |
| 10 | 0.94 | 0.87 |
| 11 | 0.81 | 0.93 |
| 12 | 0.98 | 0.93 |
| 13 |  | 0.91 |
| Average | 0.87 | 0.97 |

The epoxysilicone treated hair fibers exhibited significantly greater elasticity relative to control, demonstrating a significant reduction in damage associated with a conventional hair lightening process.

Example 10

This example demonstrates compositions of the present invention and methods of using them for treating hair damage associated with hair lightening and permanent dying processes.

Table 10A describes epoxysilicone emulsions, each of which contains either a zirconium dioxide or a titanium dioxide catalyst.

TABLE 10A

Epoxysilicone emulsions containing zirconium dioxide or titanium dioxide

| Ingredients | Formula 10A-1 | Formula 10A-2 | Formula 10A-3 | Formula 10A-4 |
|---|---|---|---|---|
| Deionized Water | 86.60 | 71.60 | 86.60 | 86.60 |
| Polysorbate 20 | 1.00 | 1.00 | 1.00 | 1.00 |
| Crodafos CES | 1.25 | 1.25 | 1.25 | 1.25 |
| Silmer ® EP Di-10 | 10.00 | 0 | 0 | 10.00 |
| Silmer ® EP J2 | 0 | 25.00 | 25.00 | 0 |
| Fragrance | 0.50 | 0.50 | 0.50 | 0.50 |
| Zirconium Dioxide | 0.05 | 0.05 | 0 | 0 |
| Titanium Dioxide | 0 | 0 | 0.05 | 0.05 |
| Optiphen | 0.50 | 0.50 | 0.50 | 0.50 |
| Sodium Benzoate | 0.10 | 0.10 | 0.10 | 0.10 |

Tables 10B and 10C describe a post-bleach shampoo and post-bleach conditioner, respectively, as follows.

TABLE 10B

Post-bleach shampoo

| Ingredients | % Weight |
|---|---|
| Deionized Water | 57.30 |
| Miranol C2MSF 40% Conc | 20.00 |
| Mackanate EL | 10.00 |
| Sandopan DTC Acid | 7.00 |
| Mackamide CPA | 3.50 |
| Elfacos GT 282S | 0.60 |
| Citric Acid Anhydrous | 0.80 |
| Fragrance | 0.30 |
| Optiphen | 0.50 |

TABLE 10C

Post-bleach conditioners

| Ingredients | Formula 10C-1 % wt | Formula 10C-2 % wt |
|---|---|---|
| DI Water | 75.460 | 73.370 |
| Polytec 95 | 0.500 | 0.500 |
| Glycerine | 2.000 | 2.000 |
| Aloe Vera Powder | 0.025 | 0.025 |
| DL-Panthenol 50% | 1.000 | 1.000 |
| Royal Jelly | 0.200 | 0.200 |
| Cetyl Alcohol | 2.560 | 2.560 |
| Crodazosoft DBQ | 3.920 | 3.920 |
| Liponate SPS | 3.000 | 3.000 |
| Konut | 5.000 | 5.000 |
| Mango Butter | 0.100 | 0.100 |
| Shea Butter | 0.875 | 0.875 |
| Tocopheryl Acetate | 0.010 | 0.010 |
| Dimethisil HNH-MV | 0.500 | 0.500 |
| Silmer ® EP J2 (Formula 3A-2) | 4.000 | 4.000 |
| Fragrance | 0.250 | 0.250 |
| Sodium Benzoate | 0.100 | 0.100 |
| Optiphen | 0.500 | 0.500 |
| Lactic Acid (88%) | 0 | 1.280 |
| Sodium Lactate (60%) | 0 | 0.310 |
| pH | 5.38 | 3.02 |

Silmer® EP-Di 10 (Siltech LLC) in combination with zirconium dioxide: 60 g of Conventional 40 Volume developer (Table 1B) and 30 g of Conventional Powder Lightener (Table 1A) were placed in a bowl and 7.5 g of micro-emulsion of Silmer® EP Di-10 (Table 10A, Formula 10A-1) were also added. This mixture was mixed well using an applicator brush until the mixture became smooth. This mixture has an active Silmer EP Di-10 of 0.769%. The components and ratios used in the bleaching composition are summarized below in Table 10D.

TABLE 10D

Bleaching composition containing epoxysilicone and zirconium dioxide

| Ingredients | Ratio | Wt % |
|---|---|---|
| Conventional Powder Lightener (Table 1A) | 30 | 30.77 |
| Conventional 40 Vol Developer (Table 1B) | 60 | 61.54 |
| Micro-emulsion Containing 10.0% Silmer ® EP Di-10 and Zirconium Dioxide (Formula 10A-1) | 7.5 | 7.69 (0.769 wt % active) |

The application procedure was as follows:
1. Untreated hair specimens were pre-tested on DMA using the ISR test.
2. The pre-tested hair fibers (Caucasian, IMHAIR) were embedded on a 4 g hair tress.
3. 32 g of bleaching mixture (Table 10D) was applied to hair embedded in the 4 g tress for 50 minutes. The hair tress was not wrapped in an Aluminum foil.
4. After 50 minutes of processing, the hair was rinsed with lukewarm water for 3 minutes.
5. 5 g of shampoo (Table 10B) was applied to the tress for 3 minutes and rinsed for 3 minutes.
6. The fibers were then treated with a conditioner (Formula 10C-1) for 10 minutes and the then rinsed with water for 3 minutes. The fibers were air-dried over night.
7. The stress at 0.50% strain was determined and the ratio of the stress (force) before and after treatment was determined by ISR.

The elasticity of the fibers after treatment with this mixture is shown in Table 10E.

TABLE 10E

ISR of fibers treated with hair lightening mixture containing Silmer ® EP Di-10 emulsion with zirconium dioxide (Formula 10A-1), Shampoo (Table 10B) and Conditioner (Formula 10C-1)

| Fiber | Un-Treated | Treated | ISR |
|---|---|---|---|
| 1 | 61.30 | 52.86 | 0.86 |
| 2 | 55.31 | 58.06 | 1.05 |
| 3 | 53.87 | 51.35 | 0.95 |
| 4 | 42.26 | 45.02 | 1.07 |
| 5 | 57.58 | 60.76 | 1.06 |
| 6 | 54.29 | 59.85 | 1.10 |
| 7 | 37.48 | 40.61 | 1.08 |
| 8 | 55.07 | 52.46 | 0.95 |
| 9 | 53.01 | 48.29 | 0.91 |
| 10 | 50.82 | 54.61 | 1.07 |
| 11 | 43.51 | 41.21 | 0.95 |
| 12 | 60.31 | 65.94 | 1.09 |
| 13 | 55.94 | 59.80 | 1.07 |
| 14 | 51.78 | 52.41 | 1.01 |
| 15 | 38.45 | 40.86 | 1.06 |
| Ave. | 51.40 | 52.27 | 1.02 |
| SD | 7.51 | 7.88 | 0.08 |
| CV | 14.61 | 15.08 | 7.37 |

The ISR of two groups of hair fibers, one treated with a conventional bleaching composition without epoxysilicone (control), and one treated with a bleaching composition containing Silmer® EP Di-10 and zirconium dioxide (Table 10D), were compared. The comparative ISR data are shown in Table 10F.

TABLE 10F

The ISR data for two fiber groups, one treated with a conventional bleaching mixture (control), and one treated with a bleaching mixture containing Silmer ® EP Di-10 and zirconium dioxide.

| Fiber | Conventional Powder Lightener (Table 1A) Plus Conventional 40 Volume Developer (Table 1B) (Control) | Powder Lightener (Table 1A), 40 Volume Developer (Table 1B), Epoxysilicone Emulsion (Formula 10A-1), Shampoo (Table 10B) and Conditioner (Formula 10C-1) |
|---|---|---|
| 1 | 0.87 | 0.86 |
| 2 | 0.85 | 1.05 |
| 3 | 0.88 | 0.95 |
| 4 | 0.91 | 1.07 |
| 5 | 0.83 | 1.06 |
| 6 | 0.82 | 1.10 |
| 7 | 0.86 | 1.08 |
| 8 | 0.83 | 0.95 |
| 9 | 0.90 | 0.91 |
| 10 | 0.94 | 1.07 |
| 11 | 0.81 | 0.95 |
| 12 | 0.98 | 1.09 |
| 13 | | 1.07 |
| 14 | | 1.01 |
| 15 | | 1.06 |
| Ave | 0.87 | 1.02 |

Silmer® EP J2 (Siltech LLC) in combination with zirconium dioxide: 60 g of Conventional 40 Volume developer (Table 1B) and 30 g of Conventional Powder Lightener (Table 1A) were placed in a bowl and 7.5 g of micro-emulsion of Silmer® EP J2 (Formula 10A-2) were also added. The mixture was mixed well using an applicator brush until the mixture became smooth. The bleaching composition had an active Silmer® EP J2 concentration of 1.923%. The components and ratios used in the bleaching composition are summarized below in Table 10G.

TABLE 10G

Bleaching composition containing epoxysilicone and zirconium dioxide

| Ingredients | Ratio | Percentage |
|---|---|---|
| Conventional Powder Lightener (Table 1A) | 30 | 30.77 |
| Conventional 40 Vol Developer (Table 1B) | 60 | 61.54 |
| Micro-emulsion Containing Silmer ® EP J2 and Zirconium Dioxide (Formula 10A-2) | 7.5 | 7.69 (1.923 wt % active) |

The application procedure was as follows:
1. Untreated hair specimens were pre-tested on DMA using the ISR test.
2. The pre-tested hair fibers (Caucasian, IMHAIR) were embedded on a 4 g hair tress.
3. 32 g of the mixture of the bleaching mixture (Table 10G) was applied to hair embedded in the 4 g tress for 50 minutes. The hair tress was not wrapped in an Aluminum foil.
4. After 50 minutes of processing, the hair was rinsed with lukewarm water for 3 minutes.
5. 5 g of Shampoo (Table 10B) was applied to the tress for 3 minutes and rinsed for 3 minutes.

6. The fibers were then treated with a conditioner (Formula 10C-1) for 10 minutes and the then rinsed with water for 3 minutes. The fibers were air-dried over night.
7. The stress at 0.50% strain was determined and the ratio of the stress (force) before and after treatment was determined by ISR.

The elasticity of the fibers before and after treatment with this mixture (Table 10G) is shown in Table 10H.

TABLE 10H

ISR of fibers treated with hair lightening mixture containing Silmer EP J2 emulsion with zirconium dioxide (Formula 10A-2), Shampoo (Table 10B) and Conditioner (Formula 10C-1)

| Fiber | Un-Treated | Treated | ISR |
|---|---|---|---|
| 1 | 47.45 | 50.17 | 1.06 |
| 2 | 58.58 | 52.73 | 0.90 |
| 3 | 65.09 | 59.77 | 0.92 |
| 4 | 51.46 | 51.64 | 1.00 |
| 5 | 59.50 | 64.26 | 1.08 |
| 6 | 52.74 | 53.64 | 1.02 |
| 7 | 61.45 | 59.14 | 0.96 |
| 8 | 50.64 | 46.19 | 0.91 |
| 9 | 53.47 | 57.47 | 1.07 |
| 10 | 48.43 | 52.38 | 1.08 |
| 11 | 41.65 | 45.86 | 1.10 |
| 12 | 57.43 | 50.95 | 0.89 |
| 13 | 45.61 | 50.05 | 1.10 |
| 14 | 48.07 | 40.62 | 0.85 |
| 15 | 52.30 | 57.81 | 1.11 |
| Ave | 52.92 | 52.85 | 1.00 |
| SD | 6.43 | 6.14 | 0.09 |
| CV | 12.15 | 11.61 | 9.06 |

The ISR of two groups of hair fibers, one treated with a conventional bleaching composition without epoxysilicone (control), and one treated with a bleaching composition containing Silmer® EP J2 and zirconium dioxide (Table 10G), were compared. The comparative ISR data are shown in Table 10 I.

TABLE 10 I

ISR data for two fiber groups, one treated with a conventional bleaching mixture (control), and one treated with a bleaching mixture containing Silmer ® EP J2 and zirconium dioxide.

| Fiber | Powder Lightener (Table 1A), 40 Volume Developer (Table 1B) (Control) | Powder Lightener (Table 1A), 40 Volume Developer (Table 1B), Epoxysilicone Emulsion (Formula 10A-2), Shampoo (Table 10B), and Conditioner (Formula 10C-1) |
|---|---|---|
| 1 | 0.87 | 1.06 |
| 2 | 0.85 | 0.90 |
| 3 | 0.88 | 0.92 |
| 4 | 0.91 | 1.00 |
| 5 | 0.83 | 1.08 |
| 6 | 0.82 | 1.02 |
| 7 | 0.86 | 0.96 |
| 8 | 0.83 | 0.91 |
| 9 | 0.90 | 1.07 |
| 10 | 0.94 | 1.08 |
| 11 | 0.81 | 1.10 |
| 12 | 0.98 | 0.89 |
| 13 | | 1.10 |
| 14 | | 0.85 |
| 15 | | 1.11 |
| Ave | 0.87 | 1.00 |

Silmer® EP J2 (Siltech LLC) in combination with titanium dioxide: 60 g of Conventional 40 Volume developer formula (Table 1B) and 30 g of Conventional Powder Lightener (Table 1A) were placed in a bowl and 7.5 g of micro-emulsion of Silmer® EP J2 (Formula 10A-3) were also added. This mixture was mixed well using an applicator brush until the mixture became smooth. The mixture had an active Silmer® EP J2 concentration of 1.923%. The components and ratios used in the bleaching composition are summarized below in Table 10J.

TABLE 10J

Bleaching composition containing epoxysilicone and titanium dioxide

| Ingredients | Ratio | Percentage |
|---|---|---|
| Conventional Powder Lightener (Table 1A) | 30 | 30.77 |
| Conventional 40 Vol Developer (Table 1B) | 60 | 61.54 |
| Micro-emulsion Containing Silmer ® EP J2 and Titanium Dioxide (Formula 10A-3) | 7.5 | 7.69 (1.923 wt % active) |

The application procedure was as follows:
1. Untreated hair specimens were pre-tested on DMA using the ISR test.
2. The pre-tested hair fibers (Caucasian, IMHAIR) were embedded on a 4 g hair tress.
3. 32 g of the mixture of the bleaching mixture (Table 10J) was applied to hair embedded in the 4 g tress for 50 minutes. The hair tress was not wrapped in an Aluminum foil.
4. After 50 minutes of processing, the hair was rinsed with lukewarm water for 3 minutes.
5. 5 g of shampoo (Table 10B) was applied to the tress for 3 minutes and rinsed for 3 minutes.
6. The fibers were then treated with a conditioner (Formula 10C-2) for 10 minutes and the then rinsed with water for 3 minutes. The fibers were air-dried over night.
7. The stress at 0.50% strain was determined and the ratio of the stress (force) before and after treatment was determined by ISR.

The elasticity of the fibers after treatment with this mixture (Table 10J) is shown in Table 10K.

TABLE 10K

ISR of fibers treated with hair lightening mixture containing Silmer ® EP J2 and titanium dioxide (Formula 10A-3), Shampoo (Table 10B), and Conditioner (Formula 10C-2)

| Fiber | Un-Treated | Treated | ISR |
|---|---|---|---|
| 1 | 54.80 | 50.39 | 0.92 |
| 2 | 82.15 | 78.56 | 0.96 |
| 3 | 66.95 | 72.86 | 1.09 |
| 4 | 60.63 | 53.79 | 0.89 |
| 5 | 74.00 | 72.25 | 0.98 |
| 6 | 57.68 | 53.74 | 0.93 |
| 7 | 56.24 | 54.77 | 0.97 |
| 8 | 68.81 | 63.60 | 0.92 |
| 9 | 66.20 | 55.16 | 0.83 |
| 10 | 62.44 | 61.36 | 0.98 |
| 11 | 61.63 | 66.14 | 1.07 |
| 12 | 77.52 | 74.03 | 0.95 |
| 13 | 53.00 | 54.27 | 1.03 |
| Ave | 64.77 | 62.38 | 0.96 |
| SD | 8.97 | 9.53 | 0.07 |
| CV | 13.86 | 15.27 | 7.38 |

The ISR of two groups of hair fibers, one treated a conventional bleaching composition without epoxysilicone (control), and one treated with a bleaching composition containing Silmer® EP J2 and titanium dioxide, were compared. The comparative ISR data are shown in Table 10L.

TABLE 10L

ISR data for two fiber groups, one treated a conventional bleaching composition (control), and one treated with a bleaching composition containing Silmer® EP J2 and titanium dioxide.

| Fiber | Conventional Powder Lightener (Table 1A), Conventional 40 Volume Developer (Table 1B) | Powder Lightener (Table 1A), 40 Volume Developer (Table 1B), Epoxysilicone Emulsion (Formula 10A-3), Shampoo (Table 10B) and Conditioner (Formula 10C-2) |
|---|---|---|
| 1 | 0.87 | 0.92 |
| 2 | 0.85 | 0.96 |
| 3 | 0.88 | 1.09 |
| 4 | 0.91 | 0.89 |
| 5 | 0.83 | 0.98 |
| 6 | 0.82 | 0.93 |
| 7 | 0.86 | 0.97 |
| 8 | 0.83 | 0.92 |
| 9 | 0.90 | 0.83 |
| 10 | 0.94 | 0.98 |
| 11 | 0.81 | 1.07 |
| 12 | 0.98 | 0.95 |
| 13 |  | 1.03 |
| 14 |  | 0.96 |
| 15 |  | 0.92 |
| Average | 0.87 | 0.96 |

Silmer® EP Di-10 (Siltech LLC) in combination with titanium dioxide: 60 g of Conventional 40 Volume developer formula (Table 1B) and 30 g of Conventional Powder Lightener (Table 1A) were placed in a bowl and 7.5 g of a micro-emulsion of Silmer EP Di-10 containing titanium dioxide (Formula 10A-4) were also added. This mixture was mixed well using an applicator brush until the mixture became smooth. The mixture had an active Silmer EP J2 concentration of 0.769%. The components and ratios used in the bleaching composition are summarized below in Table 10M.

TABLE 10M

Bleaching composition containing epoxysilicone and titanium dioxide

| Ingredients | Ratio | Percentage |
|---|---|---|
| Conventional Powder Lightener (Table 1A) | 30 | 30.77 |
| Conventional 40 Vol Developer (Table 1B) | 60 | 61.54 |
| Micro-emulsion Containing Silmer® EP Di-10 and Titanium Dioxide (Formula 10A-4) | 7.5 | 7.69 |

The application procedure was as follows:
1. Untreated hair specimens were pre-tested on DMA using the ISR test.
2. The pre-tested hair fibers (Caucasian, IMHAIR) were embedded on a 4 g hair tress.
3. 32 g of the mixture of the bleaching mixture (Table 10M) was applied to hair embedded in the 4 g tress for 50 minutes. The hair tress was not wrapped in an Aluminum foil.
4. After 50 minutes of processing, the hair was rinsed with lukewarm water for 3 minutes.
5. 5 g of shampoo (Table 10B) was applied to the tress for 3 minutes and rinsed for 3 minutes.
6. The fibers were then treated with a conditioner (Formula 10C-2) for 10 minutes and the then rinsed with water for 3 minutes. The fibers were air-dried over night.
7. The stress at 0.50% strain was determined and the ratio of the stress (force) before and after treatment was determined by ISR.

The elasticity of the fibers after treatment with this mixture (Table 10M) is shown in Table 10N.

TABLE 10N

ISR of fibers treated with hair lightening mixture containing Silmer® EP Di-10 emulsion with titanium dioxide (Formula 10A-4), Shampoo (Table 10B), and Conditioner (Formula 10C-1)

| Fiber | Un-Treated | Treated | ISR |
|---|---|---|---|
| 1 | 62.20 | 60.84 | 0.98 |
| 2 | 63.76 | 53.61 | 0.84 |
| 4 | 50.86 | 42.39 | 0.83 |
| 5 | 61.04 | 49.00 | 0.80 |
| 6 | 65.54 | 49.50 | 0.76 |
| 7 | 43.85 | 40.00 | 0.91 |
| 8 | 64.43 | 52.89 | 0.82 |
| 9 | 47.48 | 35.76 | 0.75 |
| 10 | 53.83 | 51.56 | 0.96 |
| 11 | 59.34 | 52.23 | 0.88 |
| 12 | 53.20 | 53.13 | 1.00 |
| 13 | 44.34 | 41.08 | 0.93 |
| 14 | 61.28 | 58.91 | 0.96 |
| 15 | 70.38 | 58.53 | 0.83 |
| 16 | 52.14 | 44.09 | 0.85 |
| Ave | 56.66 | 49.57 | 0.87 |
| SD | 7.94 | 7.47 | 0.08 |
| CV | 0.14 | 0.15 | 0.09 |

The ISR of two groups of hair fibers, one treated with a conventional bleaching composition without epoxysilicone (control), and one treated with a bleaching composition containing Silmer® EP Di-10 and titanium dioxide (Table 10M), were compared. The comparative ISR data are shown in Table 10 O.

TABLE 10 O

ISR data for two fiber groups, one treated with a conventional bleaching mixture (control), and one treated with a bleaching mixture containing Silmer® EP Di-10 and titanium dioxide.

| Fiber | Powder Lightener (Table 1A), 40 Volume Developer (Table 1B) (Control) | Powder Lightener (Table 1A), 40 Volume Developer (Table 1B), Epoxysilicone Emulsion (Formula 10A-4), Shampoo (Table 10B), and Conditioner (Formula 10C-1) |
|---|---|---|
| 1 | 0.87 | 0.98 |
| 2 | 0.85 | 0.84 |
| 3 | 0.88 | 0.83 |
| 4 | 0.91 | 0.80 |
| 5 | 0.83 | 0.76 |
| 6 | 0.82 | 0.91 |
| 7 | 0.86 | 0.82 |
| 8 | 0.83 | 0.75 |
| 9 | 0.90 | 0.96 |
| 10 | 0.94 | 0.88 |
| 11 | 0.81 | 1.00 |
| 12 | 0.98 | 0.93 |
| 13 |  | 0.96 |
| 14 |  | 0.83 |
| 15 |  | 0.85 |
| Average | 0.87 | 0.87 |

The epoxysilicone treated hair fibers exhibited significantly greater elasticity relative to control, demonstrating a significant reduction in damage associated with a conventional hair lightening process. The results also demonstrate that zirconium dioxide can function as an effective catalyst for Silmer® EP J2 and Silmer® EP Di-10, and titanium dioxide can function as an effective catalyst for Silmer® EP J2.

Example 11

This example demonstrates compositions of the present invention and methods of using them for treating hair damage associated with permanent waving.

Table 11A describes a conventional perming lotion (Formula 11A-1) and epoxysilicone-containing perming lotions (Formulae 11A-2 through 11A-4). Table 11B describes a neutralizing lotion.

TABLE 11A

Perming lotion compositions

| Ingredients | Formula 11A-1 (conventional) % Wt | Formula 11A-2 % Wt | Formula 11A-3 % Wt | Formula 11A-4 % Wt |
|---|---|---|---|---|
| Water Deionized | 64.960 | 58.960 | 49.96 | 55.96 |
| Versene 220 | 0.06 | 0.06 | 0.06 | 0.06 |
| Fatty Alcohol | 5.50 | 5.50 | 5.50 | 5.50 |
| Lipocol SC-20 | 3.64 | 3.64 | 3.64 | 3.64 |
| Perfecta White | 7.50 | 7.50 | 7.50 | 7.50 |
| Tennox BHA | 0.15 | 0.15 | 0.15 | 0.15 |
| Lanette 22 | 1.00 | 1.00 | 1.00 | 1.00 |
| Mazu DF 200 S | 0.02 | 0.02 | 0.02 | 0.02 |
| Ammonium Thioglycolate (60.0%) | 13.82 | 13.82 | 13.82 | 13.82 |
| Aqueous Ammonia | 3.35 | 3.35 | 3.35 | 3.35 |
| Silmer EP J2 Emulsion (Formula 3A-1) | 0.00 | 6.00 (1.5% active) | 15.00 (3.75% active) | 0.00 |
| Silmer EP Di-10 Emulsion (Table 9A) | 0.00 | 0.00 | 0.00 | 9.00 (1.35% active) |

TABLE 11B

Neutralizing lotion composition

| Ingredients | % Wt |
|---|---|
| Water | 94.52 |
| Sodium Stannate | 0.10 |
| Etidronic Acid (60%) | 0.10 |
| Hydrogen Peroxide 50% Cosmetic grade from Evonik | 5.00 |
| Sodium Dihydrogen Phosphate | 0.20 |
| Phosporic Acid (85%) | 0.08 |

A group of control hair fibers was cleansed with non-conditioning shampoo (Table 1C). The stress was determined at 0.50% strain. These fibers were dried and treated with conventional perming lotion (Table 11A) and neutralized with hydrogen peroxide neutralizer (Table 11B). The fiber elasticity (ISR) was determined at 100% RH. Each experimental group of fibers was treated with an epoxysilicone-containing perming lotion (Table 11A), and the hair fibers were neutralized with neutralizing lotion (Table 11B).

The treatment procedure for control group was as follows:
1. Untreated hair specimens were pre-tested on DMA using the ISR test.
2. The pre-tested hair fibers (Caucasian, IMHAIR) were embedded on a 2 g hair tress.
3. 8 g of the perming lotion (Formula 11A-1) was applied for 20 minutes.
4. The hair was rinsed with water for 3 minutes.
5. 8 g of neutralizing lotion (Table 11B) was applied to the tress for 5 minutes. The tress was then rinsed for 3 minutes and air-dried.
6. The stress for 0.50% strain as in step 1 and the ratio of the stress (force) were determined before and after treatment to determine the ISR.

The ISR data for the control group is shown in Table 11C.

TABLE 11C

Control Group - ISR for fibers treated with conventional perming lotion (Formula 11A-1)

| Fiber | Strength Before Treatment | Strength After Treatment | ISR |
|---|---|---|---|
| 1 | 66.39 | 55.54 | 0.84 |
| 2 | 66.83 | 49.14 | 0.74 |
| 3 | 76.63 | 59.75 | 0.78 |
| 4 | 77.29 | 60.00 | 0.78 |
| 5 | 72.24 | 51.00 | 0.71 |
| 6 | 88.12 | 63.53 | 0.72 |
| 7 | 64.19 | 49.41 | 0.77 |
| 8 | 83.60 | 67.74 | 0.81 |
| 9 | 78.42 | 55.92 | 0.71 |
| 10 | 58.29 | 43.08 | 0.74 |
| 11 | 60.37 | 44.69 | 0.74 |
| 12 | 68.85 | 57.04 | 0.83 |
| Ave | 71.77 | 54.74 | 0.76 |
| SD | 9.23 | 7.49 | 0.05 |
| CV | 12.86 | 13.68 | 5.89 |

The treatment procedure for the experimental group treated with the perming lotion of Formula 11A-2 was as follows:
1. Untreated hair specimens were pre-tested on DMA using the ISR test.
2. The pre-tested hair fibers (Caucasian, IMHAIR) were embedded on a 2 g hair tress.
3. 8 g of perming lotion (Formula 11A-2) was applied for 20 minutes.
4. The hair was rinsed with water for 3 minutes.
5. 8 g of neutralizing lotion (Table 11B) was applied to the tress for 5 minutes. The tress was then rinsed for 3 minutes and air-dried.
6. The stress for 0.50% strain as in step 1 and the ratio of the stress (force) were determined before and after treatment to determine the ISR.

The ISR data for the experimental group treated with Formula 11A-2 is shown in Table 11D.

TABLE 11D

ISR for fibers treated with Formula 11A-2 at 1.5% Active.

| Fiber | Strength Before Treatment | Strength After Treatment | ISR |
|---|---|---|---|
| 1 | 81.42 | 64.99 | 0.80 |
| 2 | 52.97 | 39.64 | 0.75 |
| 3 | 55.11 | 46.58 | 0.85 |
| 4 | 56.12 | 47.83 | 0.86 |
| 5 | 58.36 | 51.18 | 0.88 |
| 6 | 46.94 | 39.19 | 0.83 |
| 7 | 61.17 | 54.31 | 0.89 |
| 8 | 67.09 | 56.34 | 0.84 |
| 9 | 80.55 | 62.76 | 0.78 |
| 10 | 67.33 | 47.12 | 0.70 |
| 11 | 71.14 | 61.20 | 0.86 |
| 12 | 62.36 | 68.17 | 1.09 |
| 13 | 67.77 | 60.00 | 0.89 |

TABLE 11D-continued

ISR for fibers treated with Formula 11A-2 at 1.5% Active.

| Fiber | Strength Before Treatment | Strength After Treatment | ISR |
|---|---|---|---|
| 14 | 64.08 | 55.72 | 0.87 |
| Ave | 63.74 | 53.93 | 0.85 |
| SD | 9.52 | 9.00 | 0.10 |
| CV | 14.88 | 16.86 | 11.55 |

The procedure for the experimental group treated with the perming lotion of Formula 11A-3 was as follows:
1. Untreated hair specimens were pre-tested on DMA using the ISR test.
2. The pre-tested hair fibers (Caucasian, IMHAIR) were embedded on a 2 g hair tress.
3. 8 g of perming lotion (Formula 11A-3) was applied for 20 minutes.
4. Rinsed the hair was rinsed with water for 3 minutes.
5. 8 g of neutralizing lotion (Table 11B) was applied to the tress for 5 minutes. The tress was then rinsed for 3 minutes and air-dried.
6. The stress for 0.50% strain as in step 1 and the ratio of the stress (force) were determined before and after treatment to determine the ISR.

The ISR data for the experimental group treated with Formula 11A-3 is shown in Table 11E.

TABLE 11E

ISR for fibers treated with Formula 11A-3 at 3.75% active.

| Fiber | Strength Before Treatment | Strength After Treatment | ISR |
|---|---|---|---|
| 1 | 59.43 | 56.41 | 0.95 |
| 2 | 77.04 | 59.28 | 0.77 |
| 3 | 69.52 | 59.12 | 0.85 |
| 4 | 55.36 | 56.49 | 1.04 |
| 5 | 69.53 | 59.24 | 0.85 |
| 6 | 68.77 | 53.18 | 0.77 |
| 7 | 49.42 | 42.76 | 0.87 |
| 8 | 49.96 | 41.65 | 0.83 |
| 9 | 63.14 | 47.07 | 0.75 |
| 10 | 49.06 | 38.95 | 0.80 |
| 11 | 77.74 | 58.59 | 0.75 |
| 12 | 72.48 | 64.68 | 0.89 |
| 13 | 62.70 | 57.74 | 0.92 |
| Ave | 63.40 | 53.47 | 0.85 |
| SD | 10.17 | 8.13 | 0.09 |
| CV | 16.04 | 15.20 | 10.11 |

Similar testing was performed on an experimental group treated with Formula 11A-4 (Silmer® EP Di-10, 1.35% active). Table 11F compares the ISR data for the control and experimental groups.

TABLE 11F

ISR data for control and experimental groups

| Fiber | Control Group Treated with Conventional Perming Lotion (Formula 11A-1) | Experimental Group Treated With Formula 11A-2 | Experimental Group Treated With Formula 11A-3 | Experimental Group Treated With Formula 11A-4 |
|---|---|---|---|---|
| 1 | 0.84 | 0.80 | 0.95 | 0.90 |
| 2 | 0.74 | 0.75 | 0.77 | 0.89 |
| 3 | 0.78 | 0.85 | 0.85 | 0.88 |
| 4 | 0.78 | 0.86 | 1.04 | 0.79 |
| 5 | 0.71 | 0.88 | 0.85 | 0.94 |
| 6 | 0.72 | 0.83 | 0.77 | 1.05 |
| 7 | 0.77 | 0.89 | 0.87 | 0.92 |
| 8 | 0.81 | 0.84 | 0.83 | 0.81 |
| 9 | 0.71 | 0.78 | 0.75 | 0.83 |
| 10 | 0.74 | 0.70 | 0.80 | 0.78 |
| 11 | 0.74 | 0.86 | 0.75 | 0.84 |
| 12 | 0.83 | 1.09 | 0.89 | 0.89 |
| 13 | | 0.89 | 0.92 | 0.84 |
| 14 | | 0.87 | | |
| Ave | 0.76 | 0.85 | 0.85 | 0.87 |

Hair fiber elasticity for the epoxysilicone-treated groups was significantly higher than the hair fiber elasticity for the conventionally-treated control group. Adding an epoxysilicone to a conventional perming lotion can result in a significant increase in hair fiber strength relative to control.

Example 12

This example demonstrates compositions of the present invention and methods of using them for treating hair damage associated with relaxing.

Table 12A describes a conventional relaxer (Formula 12A-1) and an epoxysilicone-containing relaxer (Formulae 12A-2).

TABLE 12A

Relaxer compositions

| Ingredients | Formula 12A-1 (conventional) % Wt | Formula 12A-2 % Wt |
|---|---|---|
| Petrolatum | 23.00 | 23.00 |
| Mineral Oil | 13.50 | 13.50 |
| Emulsifying wax N.F. Croda | 10.775 | 10.775 |
| Polychol 15 | 1.00 | 1.00 |
| Solan | 0.50 | 0.50 |
| Water | 47.025 | 37.025 |
| Propylene Glycol | 2.00 | 2.00 |
| Sodium Hydroxide | 2.20 | 2.20 |
| Silmer ® EP J2 Emulsion (Formula 3A-2, 25% active)) | 0 | 10.00 (2.5% active) |

Viscosity = 34,000-54,000 cps.

A control group of hair fibers were treated with a conventional sodium hydroxide relaxer system (Formula 12A-1) and fiber elasticity (ISR) was determined at 100% RH. An experimental group of hair fibers was treated with a sodium hydroxide relaxer containing Silmer® EP J2 (Formula 12A-2).

The control group was treated as follows:
1. Untreated hair specimens were tested on DMA using the ISR test.
2. The pre-tested hair fibers (Caucasian, IMHAIR) were embedded on a 2.0 g hair tress.
3. 8.0 g of relaxer (Formula 12A-1) was applied for 18 minutes, and the tress was rinsed thoroughly for 3 minutes and towel blotted.
4. 2.5 g of non-conditioning shampoo was applied for 3 minutes and then rinsed for 3 minutes. This step was repeated for total of 2x shampoos.

5. The fibers were then rested overnight and the ISR was determined for the fibers.

The ISR data for the control group is shown in Table 12B.

TABLE 12B

ISR of fibers treated with conventional sodium hydroxide relaxer

| Fiber | Strength Before Treatment | Strength After Treatment | ISR |
|---|---|---|---|
| 1 | 86.75 | 40.93 | 0.47 |
| 2 | 85.41 | 50.78 | 0.59 |
| 3 | 63.24 | 39.13 | 0.62 |
| 4 | 56.23 | 43.63 | 0.78 |
| 5 | 66.60 | 47.55 | 0.71 |
| 6 | 63.57 | 39.75 | 0.63 |
| 7 | 73.94 | 32.45 | 0.44 |
| 8 | 80.11 | 51.33 | 0.64 |
| 9 | 55.90 | 49.78 | 0.89 |
| 10 | 61.61 | 34.64 | 0.56 |
| 11 | 63.35 | 37.28 | 0.59 |
| 12 | 60.25 | 35.73 | 0.59 |
| Ave | 68.08 | 41.90 | 0.63 |
| SD | 10.82 | 6.62 | 0.12 |
| CV (%) | 15.90 | 15.80 | 19.77 |

The same procedure was used for the experimental group treated with an epoxysilicone-containing relaxer (Formula 12A-2). The ISR data for the experimental group is provided in Table 12C.

TABLE 12C

ISR of fibers treated with sodium hydroxide relaxer containing epoxysilicone

| Fiber | Strength Before Treatment | Strength After Treatment | ISR |
|---|---|---|---|
| 1 | 48.37 | 33.04 | 0.68 |
| 2 | 54.18 | 36.26 | 0.67 |
| 3 | 59.36 | 53.87 | 0.91 |
| 4 | 44.87 | 31.82 | 0.71 |
| 5 | 68.92 | 51.34 | 0.75 |
| 6 | 58.06 | 40.09 | 0.69 |
| 7 | 52.97 | 43.69 | 0.82 |
| 8 | 66.65 | 53.54 | 0.80 |
| 9 | 53.33 | 43.74 | 0.82 |
| 10 | 59.53 | 56.10 | 0.94 |
| 11 | 53.06 | 45.90 | 0.87 |
| 12 | 67.75 | 58.94 | 0.87 |
| 13 | 69.94 | 60.37 | 0.86 |
| 14 | 48.73 | 41.41 | 0.85 |
| 15 | 67.92 | 66.25 | 0.98 |
| 16 | 60.17 | 57.87 | 0.96 |
| Ave | 58.36 | 48.39 | 0.82 |
| SD | 8.06 | 10.37 | 0.10 |
| CV (%) | 0.14 | 0.21 | 0.12 |

Table 12D compares the ISR data for the control and experimental groups.

TABLE 12D

ISR data for control and experimental groups

| Fiber | Control Group Treated With Conventional Relaxer | Experimental Group Treated With Formula 12A-2 |
|---|---|---|
| 1 | 0.47 | 0.68 |
| 2 | 0.59 | 0.67 |
| 3 | 0.62 | 0.91 |
| 4 | 0.78 | 0.71 |
| 5 | 0.71 | 0.75 |

TABLE 12D-continued

ISR data for control and experimental groups

| Fiber | Control Group Treated With Conventional Relaxer | Experimental Group Treated With Formula 12A-2 |
|---|---|---|
| 6 | 0.63 | 0.69 |
| 7 | 0.44 | 0.82 |
| 8 | 0.64 | 0.80 |
| 9 | 0.89 | 0.82 |
| 10 | 0.56 | 0.94 |
| 11 | 0.59 | 0.87 |
| 12 | 0.59 | 0.87 |
| 13 |  | 0.86 |
| 14 |  | 0.85 |
| 15 |  | 0.98 |
| 16 |  | 0.96 |
| Ave | 0.63 | 0.82 |

Hair fiber elasticity for the epoxysilicone-treated experimental group was significantly higher than the hair fiber elasticity for the conventionally-treated control group. Adding an epoxysilicone to a conventional relaxer can result in a significant increase in hair fiber strength relative to control.

Example 13

This example demonstrates compositions of the present invention and methods of using them for treating hair damage associated with permanent hair coloring with oxidative dyes. In this example, an epoxysilicone is incorporated into the color component of a permanent dye system.

Table 13A describes epoxysilicone-containing permanent hair color compositions.

TABLE 13A

Permanent hair color compositions containing epoxysilicone

| Ingredients | Formula 13A-1 % Wt. | Formula 13A-2 % Wt. |
|---|---|---|
| Water | 35.4550 | 35.4550 |
| Rapithix A-60 | 1.0000 | 1.0000 |
| Veersene 220 (Tetrasodium EDTA) | 0.9600 | 0.9600 |
| Sodium Metabisulfite | 0.3000 | 0.3000 |
| Erythorbic Acid | 0.2000 | 0.2000 |
| Cocamide DIPA | 0.5000 | 0.5000 |
| Ethoxydiglycol | 5.0000 | 5.0000 |
| Rodol Red # 9 | 3.000 | 3.000 |
| Rodol 2A3PYR | 0.200 | 0.200 |
| HC Yellow # 2 | 1.000 | 1.000 |
| Rodol D | 0.080 | 0.080 |
| Lipocol O-10 | 0.040 | 0.040 |
| Liposorb S-20 | 0.394 | 0.394 |
| Fatty Alcohol TA 1618 | 13.3000 | 13.3000 |
| Oleic Acid | 2.0000 | 2.0000 |
| Lipocol SC-20 | 2.6600 | 2.6600 |
| Carsoquat CT-429 | 2.1550 | 2.1550 |
| Lauryl Pyrrolidone | 0.5000 | 0.5000 |
| Empicol AL30/AF3 | 12.0000 | 12.0000 |
| Crodafos HCE (Oleth-5 Phosphate and Dioleyl Phosphate) | 2.0000 | 2.0000 |
| Perfume 57779M | 1.5000 | 1.5000 |
| Silmer ® EP J2 Emulsion (Formula 3A-2) | 6.2500 | 0.0000 |
| Silmere ® EP Di-10 Emulsion (Table 9A) | 0.0000 | 6.2500 |
| Monoethanolamine | 4.0000 | 4.0000 |
| Ammonium Acetate | 0.5000 | 0.5000 |
| Ammonium Hydroxide | 5.0000 | 5.0000 |

A control group of hair fibers was treated with a conventional permanent hair color 6RR (Table 7A) and a conventional hydrogen peroxide 20 volume developer (Table 7B) in accordance with Example 7 (ISR data provided in Table 7C).

An experimental group of hair fibers was treated with permanent hair color 6RR containing an epoxysilicone (Formula 13A-1) and a conventional hydrogen peroxide 20 volume developer (Table 7B). The application procedure was as follows:
1. Untreated hair specimens were pretested on DMA using the ISR test.
2. The pre-tested hair fibers (Caucasian, IMHAIR) were embedded on a 2.0 g hair tress.
3. 6 g of the mixture of 1 part of permanent color containing epoxysilicone (Formula 13A-1) and 1 part of hydrogen peroxide 20 volume developer (Table 7B) were applied for 45 minutes. The hair was not wrapped during processing.
4. The hair was rinsed with water for 3 minutes.
5. 5 g of non-conditioning shampoo (Table 1C) was applied or 3 minutes, and the fibers were rinsed for 3 minutes and air-dried.
6. The stress for 0.50% strain as in step 1 and the ratio of the stress (force) were determined before and after treatment to determine the ISR.

The ISR data for the experimental group treated with Formula 13A-1 is shown in Table 13B.

TABLE 13B

ISR data for fibers treated with permanent color 6RR containing 1.56% Silmer ® EPJ2

| Fiber | Strength Before Treatment | Strength After Treatment | ISR |
|---|---|---|---|
| 1 | 58.98 | 60.29 | 1.02 |
| 2 | 62.49 | 56.35 | 0.90 |
| 3 | 51.41 | 53.51 | 1.04 |
| 4 | 65.71 | 65.25 | 0.99 |
| 5 | 58.20 | 58.35 | 1.00 |
| 6 | 56.58 | 53.26 | 0.94 |
| 7 | 46.33 | 47.03 | 1.01 |
| 8 | 62.62 | 61.58 | 0.98 |
| 9 | 71.57 | 73.15 | 1.02 |
| 10 | 49.58 | 51.94 | 1.05 |
| 11 | 81.73 | 75.12 | 0.92 |
| 12 | 61.22 | 60.40 | 0.99 |
| 13 | 67.07 | 70.86 | 1.06 |
| 14 | 70.76 | 67.54 | 0.96 |
| 15 | 45.67 | 50.51 | 1.11 |
| Ave | 60.66 | 60.34 | 1.00 |
| SD | 10.01 | 8.58 | 0.05 |
| CV | 16.50 | 14.23 | 5.47 |

A second experimental group of hair fibers was treated with a permanent hair color 6RR containing an epoxysilicone (Formula 13A-2) and a conventional hydrogen peroxide 20 volume developer (Table 7B). The application procedure was as follows:
1. Untreated hair specimens were pre-tested on DMA using the intermittent stress relaxation test.
2. The pre-tested hair fibers (Caucasian, IMHAIR) were embedded on a 2.0 g hair tress.
3. 6 g of the mixture of 1 part of permanent color containing epoxysilicone (Formula 13A-2) and 1 part of hydrogen peroxide 20 volume developer (Table 7B) were applied for 45 minutes. The hair was not wrapped during processing.
4. The hair was rinsed with water for 3 minutes.
5. 5 g of non-conditioning shampoo (Table 1C) was applied for 3 minutes, and the fibers were rinsed for 3 minutes and air-dried.
6. The stress for 0.50% strain as in step 1 and the ratio of the stress (force) were determined before and after treatment to determine the ISR.

The ISR data for the fibers treated with Formula 13A-2 is shown in Table 13C.

TABLE 13C

ISR Data for fibers treated with permanent color 6RR containing 1.56% Silmer ® EP Di-10

| Fiber | Strength Before Treatment | Strength After Treatment | ISR |
|---|---|---|---|
| 1 | 68.24 | 66.62 | 0.98 |
| 2 | 79.18 | 72.76 | 0.92 |
| 3 | 92.52 | 90.24 | 0.97 |
| 4 | 75.78 | 59.69 | 0.79 |
| 5 | 50.56 | 52.71 | 1.04 |
| 6 | 66.01 | 67.69 | 1.03 |
| 7 | 69.39 | 62.45 | 0.90 |
| 8 | 58.59 | 62.46 | 1.07 |
| 9 | 67.56 | 70.35 | 1.04 |
| 10 | 63.03 | 67.63 | 1.07 |
| 11 | 57.77 | 64.60 | 1.12 |
| 12 | 53.81 | 42.51 | 0.79 |
| 13 | 60.90 | 61.44 | 1.01 |
| 14 | 54.35 | 55.72 | 1.02 |
| 15 | 57.47 | 61.19 | 1.06 |
| Ave | 65.01 | 63.87 | 0.99 |
| SD | 11.12 | 10.47 | 0.10 |
| CV | 17.10 | 16.39 | 10.13 |

The ISR data for the control and experimental groups are compared in Table 13D.

TABLE 13D

ISR for creme color 6RR system - conventional and with epoxysilicone

| Fiber | ISR of Control Group Treated with Conventional Permanent Color System | ISR of Experimental Group Treated with Permanent Color System Containing Silmer ® EP J2 in Color Component | ISR of Experimental Group Treated with Permanent Color Containing Silmer ® EP Di-10 in Color Componente |
|---|---|---|---|
| 1 | 0.93 | 1.02 | 0.98 |
| 2 | 0.93 | 0.90 | 0.92 |
| 3 | 0.94 | 1.04 | 0.97 |
| 4 | 0.74 | 0.99 | 0.79 |
| 5 | 0.76 | 1.00 | 1.04 |
| 6 | 0.83 | 0.94 | 1.03 |
| 7 | 0.77 | 1.01 | 0.90 |
| 8 | 0.93 | 0.98 | 1.07 |
| 9 | 0.97 | 1.02 | 1.04 |
| 10 | 0.96 | 1.05 | 1.07 |
| 11 | 0.74 | 0.92 | 1.12 |
| 12 | 1.01 | 0.99 | 0.79 |
| 13 | | 1.06 | 1.01 |
| 14 | | 0.96 | 1.02 |
| 15 | | 1.11 | 1.06 |
| Ave | 0.88 | 1.00 | 0.99 |

The ISR of control group was significantly lower than both experimental groups for which the permanent colors contained epoxysilicone. The incorporation of epoxysilicone into the permanent hair color base resulted in a significant increase in fiber elasticity, indicating that the hair fibers were strengthened with almost no damage resulting from permanent hair coloring with oxidative dyes.

Example 14

This example demonstrates a composition of the present invention and its effectiveness in treating hair damage associated with smoothing treatments.

A control group of fibers was treated with Uberliss® Hydrating Shampoo, Uberliss® Fiber Expander, Uberliss® Fiber Restructure, and flat ironing. The application procedure for control fibers was as follows:
1. Hair specimens (Caucasian, IMHAIR) were pre-tested on DMA using the ISR test.
2. The pre-tested fibers were embedded onto a 2 g hair tress.
3. 0.66 g of Uberliss® Hydrating Shampoo, lot #16A0701, was applied for 3 minutes and then rinsed for 3 minutes.
4. 0.40 g of Uberliss® Expander, lot #16A1404, was applied.
5. The sample was covered with plastic wrap for 10 minutes and the wrap was removed.
6. 0.80 g of Uberliss® Fiber Restructuring straightener, lot #16A1502, was applied. The sample was covered with plastic saran wrap and put under an overhead dryer for 20 minutes at high setting.
7. The plastic wrap was removed (no rinsing).
8. 0.40 g of Uberliss® Nutritive Mask, lot #16A0703, was applied. The sampled was covered with plastic wrap and put under the dryer for 10 minutes.
9. The plastic wrap was removed and the hair was allowed to cool down for 5 minutes, rinsed for 5 seconds, and blow dried.
10. 0.25 g of KeraCare® Thermal Wonder 6-in-1 Styler was applied.
11. The hair was flat ironed by passing 7 times at 450° F.
12. The hair was allowed to sit overnight before testing.

The ISR data for the control group fibers is shown in Table 17A.

TABLE 17A

ISR for control group treated with Uberliss® Smoothing Treatment

| Fiber | Untreated Fiber Strength | Treated Fiber Strength | ISR |
|---|---|---|---|
| 1 | 72.54 | 52.09 | 0.72 |
| 2 | 67.97 | 52.91 | 0.78 |
| 3 | 56.60 | 45.00 | 0.79 |
| 4 | 43.60 | 39.55 | 0.91 |
| 5 | 61.30 | 48.41 | 0.79 |
| 6 | 64.99 | 52.01 | 0.80 |
| 7 | 77.88 | 62.51 | 0.81 |
| 8 | 71.47 | 52.02 | 0.73 |
| 9 | 57.21 | 50.34 | 0.88 |
| 10 | 57.03 | 54.46 | 0.96 |
| 11 | 70.36 | 57.33 | 0.81 |
| 12 | 57.40 | 45.61 | 0.79 |
| 13 | 67.64 | 49.49 | 0.73 |
| Ave | 63.54 | 50.90 | 0.81 |
| SD | 9.15 | 5.75 | 0.07 |
| CV (%) | 14.41 | 11.30 | 8.79 |

An experimental group of fibers was treated with Uberliss® Fiber Restructure containing an epoxysilicone, the composition of which is shown in Table 17B.

TABLE 17B

Uberliss® Fiber Restructure containing epoxysilicone

| Product | Amount (g) | Wt % |
|---|---|---|
| Uberliss® Fiber Restructure | 120.00 | 96.97 |
| Silmer® EP J2 Emulsion (Formula 3A-2) | 3.75 | 3.03 |

The application procedure for the experimental group was as follows:
1. Hair specimens (Caucasian, IMHAIR) were pre-tested on DMA using the ISR test.
2. The pre-tested fibers were embedded onto a 2 g hair tress.
3. 0.66 g of Uberliss® Hydrating Shampoo, lot #16A0701, was applied for 3 minutes, and the hair was rinsed for 3 minutes.
4. 0.40 g of Uberliss® Expander, lot #16A1404, was applied.
5. The sample was covered with plastic wrap for 10 minutes, and the wrap was removed.
6. 0.80 g of Uberliss® Fiber Restructuring straightener, lot #16A1502, containing epoxysilicone (Table 17B) was applied. The sample was covered with plastic saran wrap, and put under an overhead dryer for 20 minutes at high setting.
7. The plastic wrap was removed (no rinsing).
8. 0.40 g of Uberliss® Nutritive Mask, lot #16A0703, was applied The sample was covered with plastic wrap and put under the dryer for 10 minutes.
9. The plastic wrap was removed and the hair was allowed to cool down for 5 minutes, rinsed for 5 seconds, and blow dried.
10. 0.25 g of KeraCare® Thermal Wonder 6-in-1 Styler was applied.
13. The hair was flat ironed by passing 7 times at 450° F.
11. The hair was allowed to sit overnight before testing.

The ISR data for the experimental group is provided in Table 17C.

TABLE 17C

ISR for experimental group treated with Uberliss® Smoothing Treatment containing epoxysilicone (0.76% active)

| Fiber | Stress Before Treatment (g/denier) | Stress After Treatment (g/denier) | ISR |
|---|---|---|---|
| 1 | 65.15 | 47.87 | 0.73 |
| 2 | 54.92 | 42.25 | 0.77 |
| 3 | 60.99 | 45.16 | 0.74 |
| 4 | 40.11 | 43.73 | 1.09 |
| 5 | 61.29 | 59.39 | 0.97 |
| 6 | 67.26 | 54.57 | 0.81 |
| 7 | 60.67 | 51.93 | 0.86 |
| 8 | 72.81 | 67.34 | 0.92 |
| 9 | 63.24 | 66.28 | 1.05 |
| 10 | 45.16 | 45.16 | 1.00 |
| 13 | 49.64 | 50.25 | 1.01 |
| 14 | 62.23 | 50.65 | 0.81 |
| 15 | 71.12 | 62.22 | 0.87 |
| 16 | 58.38 | 48.57 | 0.83 |
| Ave | 59.50 | 52.53 | 0.89 |
| SD | 9.34 | 8.28 | 0.12 |
| CV | 0.16 | 0.16 | 0.13 |

The ISR of the experimental group treated with epoxysilicone was significantly higher than that of the control group. The addition of epoxysilicone to the Uberliss®

Smoothing Treatment system resulted in a significant increase in elasticity of the hair fibers.

Example 15

This example demonstrates a composition of the present invention and its effectiveness in treating hair damage associated with permanent dying. In this example, an epoxysilicone is incorporated into the hydrogen peroxide developer component of a permanent color system.

A control group of hair fibers was treated with a conventional permanent hair color 6RR (Table 7A) and a conventional hydrogen peroxide 20 volume developer (Table 7B) in accordance with Example 7 (ISR data provided in Table 7C).

An experimental group of hair fibers was treated with conventional permanent hair color 6RR (Table 7A) and a hydrogen peroxide 20 volume developer containing an epoxysilicone. The composition of the epoxysilicone-containing hydrogen peroxide 20 volume developer is provided in Table 15A.

TABLE 15A hydrogen peroxide 20 volume developer containing epoxysilicone

| Ingredient Name | % Wt. |
| --- | --- |
| Water | 73.54 |
| Etidronic Acid (60%) | 0.10 |
| Sodium Stannate | 0.10 |
| Lipocol-C (Cetyl Alcohol) | 3.50 |
| Procol CA-10 | 1.50 |
| Anti Foam A Compound | 0.05 |
| Carsoquat CT-429 | 2.50 |
| Aculyn 46 Polymer | 0.21 |
| Hydrogen Peroxide 50% (FMC) | 12.00 |
| Silmer EP Di-10 Emulsion (Table 9A, 15.0% active) | 6.25 |
| Phosphoric Acid (85%) | 0.05 |
| Sodium Dihydrogen Phosphate | 0.20 |

The application procedure was as follows:
1. Untreated hair specimens were pre-tested on DMA using the ISR test.
2. The pre-tested hair fibers (Caucasian, IMHAIR) were embedded on a 2.0 g hair tress.
3. 6 g of a mixture of 1 part of conventional permanent color (Table 7A) and 1 part of the epoxysilicone-containing 20 volume developer (Table 15A) was applied for 45 minutes. The hair was not wrapped during processing.
4. The hair was rinsed with water for 3 minutes.
5. 5 g of non-conditioning shampoo (Table 1C) was applied for 3 minutes, and the hair fibers were rinsed for 3 minutes and air-dried.
6. The stress for 0.50% strain as in step 1 and the ratio of the stress (force) before and after treatment were determined to determine the ISR.

The ISR for the experimental group was shown in Table 15B.

TABLE 15B

ISR of experimental group treated with hydrogen peroxide 20 volume developer containing epoxysilicone

| Fiber | Before Treatment | After Treatment | ISR |
| --- | --- | --- | --- |
| 1 | 63.18 | 60.95 | 0.96 |
| 2 | 66.30 | 65.22 | 0.98 |
| 3 | 62.00 | 59.09 | 0.95 |
| 4 | 72.19 | 58.20 | 0.81 |
| 5 | 66.58 | 69.96 | 1.05 |
| 6 | 55.38 | 56.50 | 1.02 |
| 7 | 63.18 | 64.99 | 1.03 |
| 8 | 55.47 | 51.39 | 0.93 |
| 9 | 69.86 | 70.69 | 1.01 |
| 10 | 60.57 | 58.12 | 0.96 |
| 11 | 54.73 | 61.79 | 1.13 |
| 12 | 73.53 | 55.59 | 0.76 |
| 13 | 62.18 | 69.51 | 1.12 |
| 14 | 73.27 | 75.30 | 1.03 |
| 15 | 71.63 | 70.39 | 0.98 |
| Ave | 64.67 | 63.18 | 0.98 |
| SD | 6.52 | 6.89 | 0.10 |
| CV | 10.08 | 10.90 | 10.17 |

The ISRs of the control and experimental groups are compared in Table 15C.

TABLE 15C

ISR of control and experimental groups

| Fiber | ISR of Control Group Treated With Conventional Permanent Color System | ISR of Experimental Group Treated With Permanent Color System Containing Epoxysilicone in Developer Component |
| --- | --- | --- |
| 1 | 0.93 | 0.96 |
| 2 | 0.93 | 0.98 |
| 3 | 0.94 | 0.95 |
| 4 | 0.74 | 0.81 |
| 5 | 0.76 | 1.05 |
| 6 | 0.83 | 1.02 |
| 7 | 0.77 | 1.03 |
| 8 | 0.93 | 0.93 |
| 9 | 0.97 | 1.01 |
| 10 | 0.96 | 0.96 |
| 11 | 0.74 | 1.13 |
| 12 | 1.01 | 0.76 |
| 13 | | 1.12 |
| 14 | | 1.03 |
| 15 | | 0.98 |
| Ave | 0.88 | 0.98 |

When an epoxysilicone was incorporated into the hydrogen peroxide developer component of a conventional permanent color system, the elasticity of the hair fibers increased significantly relative to control.

Example 16

This example demonstrates a composition of the present invention and its effectiveness in treating hair damage associated with bleaching.

A first control group of untreated fibers was subjected to repeated brushing, and broken fibers were collected after every 400 strokes. A second control group of fibers was treated with a conventional bleaching composition, as follows:
1. A conventional powder bleach composition (Table 1A, 30 g) and a conventional 40-volume developer (Table 1B, 60 g) were combined and mixed well.
2. 32 g of this mixture was applied to a 4 g hair tress and the tress was allowed to sit for 50 minutes.

3. The hair was rinsed with water.
4. 5 g of a non-conditioning shampoo (Table 1C) was applied for 3 min and the hair was rinsed for 3 minutes.
5. The tress was towel blotted and air dried.
6. The tresses were allowed to equilibrate over night at 45% RH.
7. Tresses were then subjected to repeated brushing with a brushing machine as shown in FIG. 1.

An experimental group of fibers was treated with a bleaching composition containing an epoxysilicone (Table 3D), as follows:

1. 32 g of a bleaching composition containing an epoxysilicone (Table 3D) was applied to a 4 g hair tress and the tress was allowed to sit for 50 minutes.
2. The hair was rinsed with water.
3. 5 g of Non-conditioning shampoo (Table 1C) was applied for 3 min and the hair was rinsed for 3 minutes.
4. The hair was towel blotted and air dried.
5. The tresses were allowed to equilibrate overnight at 45% RH.
6. The tresses were then subjected to repeated brushing with a brushing machine as shown in FIG. 1.

The data for broken fibers for all three groups is shown in Table 16A.

TABLE 16A

Average number of broken fibers for each group for every 400 brush strokes

| No. of Strokes | Broken Fibers for Untreated Control Group | Broken Fibers for Conventionally Bleached Control Group | Broken Fibers for Group Treated with Bleaching Composition Containing Epoxysilicone |
|---|---|---|---|
| 400 | 6.5 | 7.5 | 3.5 |
| 800 | 4.3 | 6.5 | 1.5 |
| 1200 | 3.3 | 5.5 | 3.8 |
| 1600 | 4.3 | 5 | 2.3 |
| 2000 | 4.8 | 7 | 2.3 |
| 2400 | 1.5 | 6.8 | 2.3 |
| 2800 | 0 | 3.8 | 1.3 |
| 3200 | 1.8 | 3.8 | 1.8 |
| 3600 | 3 | 5 | 3.3 |
| 4000 | 1 | 4.3 | 1 |
| 4400 | 0.8 | 4.5 | 1.3 |
| 4800 | 0.5 | 3 | 1 |
| 5200 | 1.5 | 3.5 | 1.5 |
| 5600 | 1 | 4.5 | 0.5 |
| 6000 | 1.3 | 7 | 1 |
| 6400 | 1.5 | 3.3 | 0.8 |
| 6800 | 1 | 3.5 | 1.5 |
| 7200 | 0.8 | 2.5 | 1 |
| 7600 | 3.5 | 2.8 | 0.5 |
| 8000 | 1.5 | 4 | 0.5 |
| 8400 | 1.8 | 4.8 | 0.8 |
| 8800 | 0.8 | 6.5 | 1.8 |
| 9200 | 1.8 | 2 | 1.3 |
| 9600 | 2.3 | 2 | 1.3 |
| 10000 | 1.3 | 4.8 | 0.8 |
| Total | 51.3 | 113.5 | 38 |
| Ave | 2.076 | 4.556 | 1.548 |

Upon repeated brushing, the average breakage of fibers per 400 stokes for untreated fibers was 2.0760. For the conventionally bleached hair fibers, the average breakage of fibers per 400 strokes was 4.5560. For the experimental group bleached with a bleaching composition containing an epoxysilicone, the average breakage of fibers per 400 strokes was 1.5480. The experimental group exhibited the least amount of breakage. These results were surprising, as the average breakage of fibers for the group treated with bleaching composition containing epoxysilicone was even less than the average breakage for the untreated fibers. The fibers treated with the bleaching composition containing epoxysilicone had greater resistance to fatigue upon repeated brushing relative to control.

Example 17

This example demonstrates a composition of the present invention and its effectiveness in treating hair damage associated with bleaching.

Untreated fiber tresses and treated fiber tresses bleached with a bleaching mixture containing an epoxysilicone (Table 3D) were shampooed 1, 5, 10, 15, and 20 times at 40% RH, and the moisture contents for each tress were determined using microwave resonance (FIG. 2). The results are shown in Table 17A.

TABLE 17A

Moisture contents of untreated hair and hair treated with epoxysilicone containing bleaching mixture (Table 3D) and shampoo at 40% RH

| Untreated | Treated + 1 Shampoo | Treated + 5 Shampoos | Treated + 10 Shampoos | Treated + 15 Shampoos | Treated + 20 Shampoos |
|---|---|---|---|---|---|
| 8.433 | 8.715 | 8.035 | 8.511 | 8.149 | 8.13 |
| 8.476 | 8.182 | 8.301 | 8.283 | 8.45 | 8.201 |
| 8.428 | 8.274 | 8.101 | 8.355 | 8.176 | 8.401 |
| 8.449 | 8.311 | 8.38 | 8.412 | 8.12 | 8.351 |

No significant difference in moisture content was observed between untreated and treated fibers even after repeated shampoos at 40% RH.

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and "at least one" and similar referents in the context of describing the invention (especially in the context of the following claims) are to be construed to cover both the singular and the plural, unless otherwise indicated herein or clearly contradicted by context. The use of the term "at least one" followed by a list of one or more items (for example, "at least one of A and B") is to be construed to mean one item selected from the listed items (A or B) or any combination of two or more of the listed items (A and B), unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

The invention claimed is:

1. A method for treating hair damage, the method comprising contacting the hair with an effective amount of at least one compound of formula (I):

$$R^5-\underset{\underset{R^2}{|}}{\overset{\overset{R^1}{|}}{Si}}-\left[O-\underset{\underset{(CH_2)_3}{|}}{\overset{\overset{CH_3}{|}}{Si}}\right]_a-\left[O-\underset{\underset{CH_3}{|}}{\overset{\overset{(CH_2)_3-O-A-H}{|}}{Si}}\right]_b-\left[O-\underset{\underset{CH_3}{|}}{\overset{\overset{CH_3}{|}}{Si}}\right]_c-O-\underset{\underset{R^4}{|}}{\overset{\overset{R^3}{|}}{Si}}-R^6 \quad (I)$$

with $O-CH_2-CH\underset{O}{\overset{\diagdown\diagup}{-}}CH_2$ wherein:

$R^1$-$R^4$ are methyl;

$R^5$ and $R^6$ are the same or different and each is $C_{1-26}$ alkyl or a substituent of the formula:

$$(CH_2)_3-O-CH_2-CH\underset{O}{\overset{\diagdown\diagup}{-}}CH_2;$$

A is selected from one or more of $(CH_2-CH_2-O)_x$, $(CH(CH_3)-CH_2-O)_y$, and $(CH_2-CH(CH_3)-O)_z$, wherein x, y, and z are the same or different and each is from 0-20, provided that at least one of x, y, or z is 1;

a is from 0-20;

b is from 0-20; and c is from 0-30, provided that c is at least 1 and, when a is 0, then at least one of $R^5$ and $R^6$ is a substituent of the formula:

$$(CH_2)_3-O-CH_2-CH\underset{O}{\overset{\diagdown\diagup}{-}}CH_2.$$

2. The method of claim 1, wherein a is at least 1.

3. The method of claim 1, wherein $R^5$ and $R^6$ are methyl, and a is at least 1.

4. The method of claim 1, wherein a is from 1-15, b is from 0-15, and c is from 1-30.

5. The method of claim 1, wherein b is at least 1.

6. The method of claim 5, wherein A is $(CH_2-CH_2-O)_x$.

7. The method of claim 6, wherein x is from 8-20.

8. The method of claim 7, wherein x is from 4-12.

9. The method of claim 1, wherein a and b are both zero.

10. The method of claim 1, wherein a and b are at least 1.

11. The method of claim 10, wherein the compound of formula (I) is selected from one or more of the following:

$$H_3C-\underset{\underset{CH_3}{|}}{\overset{\overset{CH_3}{|}}{Si}}-O-\underset{\underset{(CH_2)_3}{|}}{\overset{\overset{CH_3}{|}}{Si}}-\left[O-\underset{\underset{CH_3}{|}}{\overset{\overset{(CH_2)_3-O-(CH_2CH_2O)_8-H}{|}}{Si}}\right]_3-\left[O-\underset{\underset{CH_3}{|}}{\overset{\overset{CH_3}{|}}{Si}}\right]_8-O-\underset{\underset{CH_3}{|}}{\overset{\overset{CH_3}{|}}{Si}}-CH_3, \text{ and} \quad (Ia)$$

with $O-CH_2-CH\underset{O}{\overset{\diagdown\diagup}{-}}CH_3$ $$H_3C-\underset{\underset{CH_3}{|}}{\overset{\overset{CH_3}{|}}{Si}}-\left[O-\underset{\underset{(CH_2)_3}{|}}{\overset{\overset{CH_3}{|}}{Si}}\right]_2-\left[O-\underset{\underset{CH_3}{|}}{\overset{\overset{(CH_2)_3-O-(CH_2CH_2O)_8-H}{|}}{Si}}\right]_9-\left[O-\underset{\underset{CH_3}{|}}{\overset{\overset{CH_3}{|}}{Si}}\right]_{10}-O-\underset{\underset{CH_3}{|}}{\overset{\overset{CH_3}{|}}{Si}}-CH_3. \quad (Ib)$$

with $O-CH_2-CH\underset{O}{\overset{\diagdown\diagup}{-}}CH_3$

12. The method of claim 1, wherein a is at least 1 and b is 0.

13. The method of claim 12, wherein the compound of formula (I) is selected from one or more of the following:

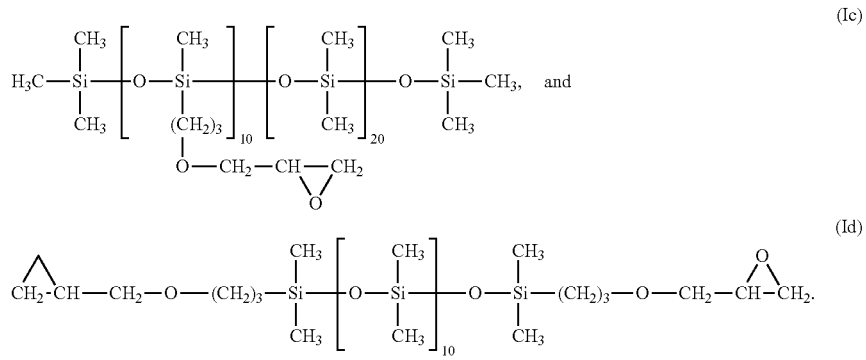

14. The method of claim 1, wherein the hair damage is caused by chemical damage, sunlight, air oxidation, mechanical stress, or a combination thereof.

15. The method of claim 14, wherein the hair damage is caused by a hair altering process that is capable of damaging hair fibers.

16. The method of claim 15, wherein the hair altering process comprises applying an oxidative hair lightening agent to the hair.

17. The method of claim 16, wherein the compound of formula (I) and the oxidative hair lightening agent are combined before application to the hair.

18. The method of claim 17, wherein the concentration of the compound of formula (I) is from about 0.1 wt % to about 10 wt % after being combined with the oxidative hair lightening agent.

19. The method of claim 16, wherein the oxidative hair lightening agent is prepared by combining at least one persulfate and at least one peroxide.

20. The method of claim 19, wherein the persulfate comprises potassium persulfate, ammonium persulfate, or a combination thereof.

21. The method of claim 19, wherein the peroxide comprises hydrogen peroxide.

22. The method of claim 15, wherein the hair altering process comprises applying a hair relaxing agent to the hair.

23. The method of claim 22, wherein the compound of formula (I) and the hair relaxing agent are combined before application to the hair.

24. The method of claim 23, wherein the concentration of the compound of formula (I) is from about 0.1 wt % to about 10 wt % after being combined with the hair relaxing agent.

25. The method of claim 22, wherein the hair relaxing agent is prepared by combining at least one metal hydroxide and at least one alkaline salt of guanidine.

26. The method of claim 25, wherein the metal hydroxide comprises calcium hydroxide.

27. The method of claim 25, wherein the alkaline salt of guanidine comprises guanidine carbonate.

28. The method of claim 15, wherein the hair altering process comprises applying to the hair an oxidative hair dyeing agent.

29. The method of claim 28, wherein the compound of formula (I) and the oxidative hair dyeing agent are combined before application to the hair.

30. The method of claim 29, wherein the concentration of the compound of formula (I) is from about 0.1 wt % to about 10 wt % after being combined with the oxidative hair dyeing agent.

31. The method of claim 28, wherein the oxidative hair dyeing agent is prepared by combining at least one permanent hair dyeing agent with at least one peroxide.

32. The method of claim 31, wherein the permanent hair dyeing agent comprises two or more permanent hair dyes.

33. The method of claim 31, wherein the peroxide comprises hydrogen peroxide.

34. The method of claim 14, wherein the compound of formula (I) is of the formula:

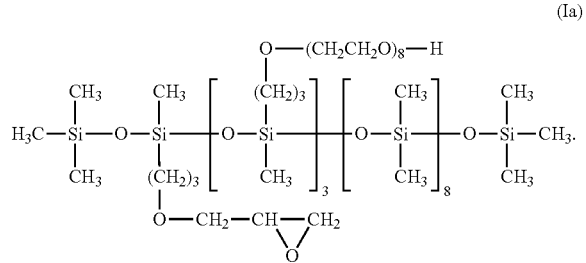

35. The method of claim 14, wherein the compound of formula (I) is selected from one or more of the following:

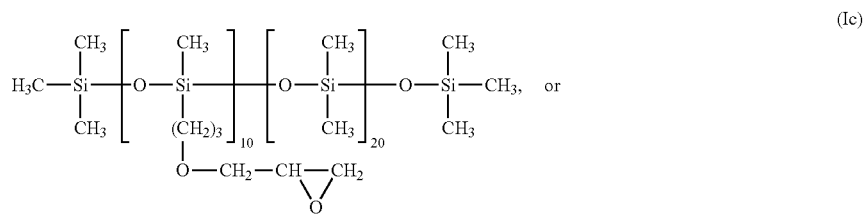

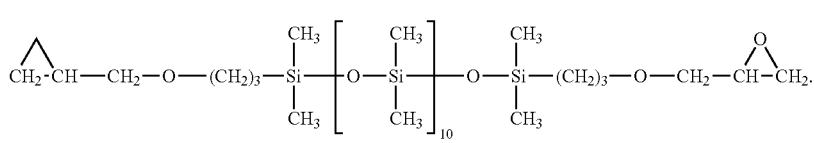

(Id)

36. The method of claim 35, wherein the compound of formula (I) is in the form of an aqueous emulsion.

37. A product comprising:
a hair damage treating effective amount of at least one compound of formula (I):

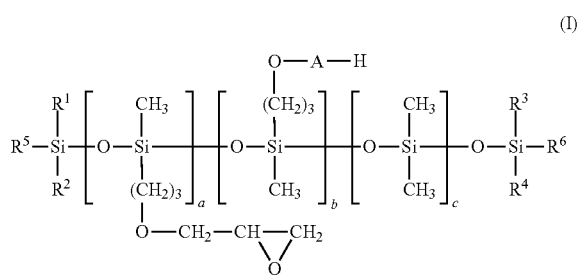

(I)

wherein:
$R^1$-$R^4$ are methyl;
$R^5$ and $R^6$ are the same or different and each is $C_{1-26}$ alkyl or a substituent of the formula:

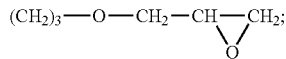

A is selected from one or more of $(CH_2—CH_2—O)_x$, $(CH(CH_3)—CH_2—O)_y$, and $(CH_2—CH(CH_3)—O)_z$, wherein x, y, and z are the same or different and each is from 0-20, provided that at least one of x, y, or z is 1;
a is from 0-20;
b is from 0-20; and
c is from 0-30,
provided that c is at least 1 and, when a is 0, then at least one of $R^5$ and $R^6$ is a substituent of the formula:

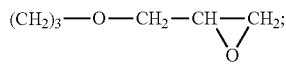

and
instructions for applying the compound of formula (I) to the hair.

38. The product of claim 37, wherein the compound of formula (I) is formulated in combination with a carrier.

39. The product of claim 38, wherein the carrier is a liquid vehicle.

40. The product of claim 37, further comprising:
a hair altering agent capable of damaging hair fibers; and
instructions for applying the hair altering agent to the hair.

41. The product of claim 40, wherein the hair altering agent is selected from oxidative hair lightening agents, hair relaxing agents, and oxidative hair dyeing agents.

42. The product of claim 40, further comprising instructions for combining the hair altering agent and the compound of formula (I) before application to the hair.

43. The product of claim 37, wherein the compound of formula (I) is soluble in water.

44. The product of claim 43, wherein the compound of formula (I) is formulated as an aqueous solution.

45. The product of claim 44, wherein the compound of formula (I) is of the formula:

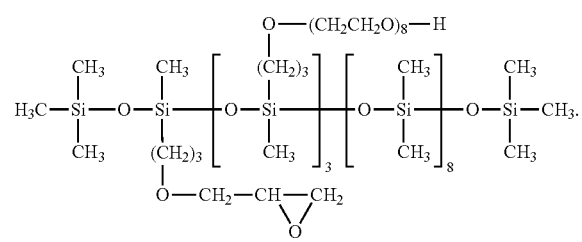

(Ia)

46. The product of claim 37, wherein the compound of formula (I) is insoluble in water.

47. The product of claim 46, wherein the compound of formula (I) is formulated as an aqueous emulsion.

48. The product of claim 47, wherein the aqueous emulsion comprises from about 2 wt % to about 75 wt % of the compound of formula (I).

49. The product of claim 47, wherein the aqueous emulsion comprises from about 5 wt % to about 50 wt % of the compound of formula (I).

50. The product of claim 47, wherein the aqueous emulsion comprises from about 10 wt % to about 30 wt % of the compound of formula (I).

51. The product of claim 47, wherein the aqueous emulsion comprises about 25 wt % of the compound of formula (I).

52. The product of claim 46, wherein the compound of formula (I) is of the formula:

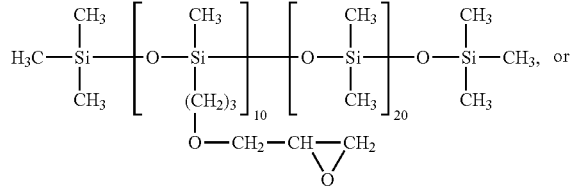

(Ic)

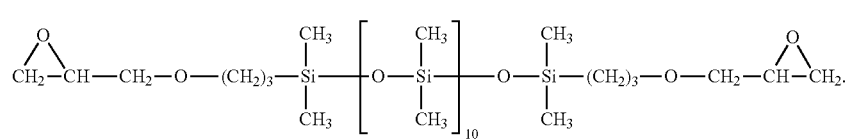
(Id)